United States Patent
Shelton, IV et al.

(10) Patent No.: US 11,864,765 B2
(45) Date of Patent: *Jan. 9, 2024

(54) COMPRESSIBLE ADJUNCTS WITH FLUID CONTROL FEATURES

(71) Applicant: Cilag GmbH International, Zug (CH)

(72) Inventors: Frederick E. Shelton, IV, Hillsboro, OH (US); Jason L. Harris, Lebanon, OH (US); Michael J. Vendely, Lebanon, OH (US); Christopher Q. Seow, Cincinnati, OH (US); Heather Strang, West Chester, OH (US); Jordan B. Wong, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 332 days.

This patent is subject to a terminal disclaimer.

(21) Appl. No.: 17/216,977

(22) Filed: Mar. 30, 2021

(65) Prior Publication Data
US 2022/0313257 A1 Oct. 6, 2022

(51) Int. Cl.
*A61B 17/072* (2006.01)
*A61K 9/00* (2006.01)

(52) U.S. Cl.
CPC ...... *A61B 17/07292* (2013.01); *A61K 9/0024* (2013.01); *A61B 2017/07257* (2013.01); *A61B 2017/07271* (2013.01)

(58) Field of Classification Search
CPC .............................................. A61B 17/07292
See application file for complete search history.

(56) References Cited

U.S. PATENT DOCUMENTS 5,711,960 A 1/1998 Shikinami
5,833,695 A 11/1998 Yoon
(Continued)

FOREIGN PATENT DOCUMENTS

EP 2113206 A2 11/2009
EP 2333701 A1 6/2011
(Continued)

OTHER PUBLICATIONS

International Patent Application No. PCT/IB2020/060710 entitled "Drug Delivery Device Sensing Modules", filed on Nov. 13, 2020, 100 pages.
(Continued)

*Primary Examiner* — Gloria R Weeks
(74) *Attorney, Agent, or Firm* — Mintz Levin Cohn Ferris Glovsky and Popeo, P.C.

(57) ABSTRACT

Compressible adjuncts for use with a surgical cartridge are provided. In one exemplary embodiment, a compressible adjunct includes a biocompatible adjunct material that is configured to be releasably retained on a staple cartridge and that is configured to be delivered to tissue by deployment of staples in the cartridge. The adjunct material includes a lattice main structure having at least one absorbable sub-structure formed in the lattice main structure, the at least one absorbable sub-structure configured to control fluid movement through the adjunct material such that the fluid movement impacts healing of tissue adjacent the adjunct material when the adjunct material is in a tissue deployed state. Stapling assemblies for use with a surgical stapler are also provided.

14 Claims, 16 Drawing Sheets

(56) References Cited

U.S. PATENT DOCUMENTS

| | | | |
|---|---|---|---|
| 6,029,671 A | 2/2000 | Stevens et al. | |
| 7,143,925 B2 | 12/2006 | Shelton, IV et al. | |
| 7,601,118 B2 | 10/2009 | Smith et al. | |
| 8,062,330 B2* | 11/2011 | Prommersberger | B29C 39/123 |
| | | | 606/151 |
| 8,317,070 B2 | 11/2012 | Hueil et al. | |
| 8,393,514 B2 | 3/2013 | Shelton, IV et al. | |
| 8,864,007 B2 | 10/2014 | Widenhouse et al. | |
| 9,084,602 B2 | 7/2015 | Gleiman | |
| 9,232,941 B2 | 1/2016 | Mandakolathur et al. | |
| 9,272,406 B2 | 3/2016 | Aronhalt et al. | |
| 9,282,962 B2 | 3/2016 | Schmid et al. | |
| 9,301,753 B2* | 4/2016 | Aldridge | A61B 17/00491 |
| 9,480,476 B2 | 11/2016 | Aldridge et al. | |
| 9,681,936 B2 | 6/2017 | Hodgkinson et al. | |
| 9,913,642 B2 | 3/2018 | Leimbach et al. | |
| 9,999,408 B2 | 6/2018 | Boudreaux et al. | |
| 10,111,661 B2* | 10/2018 | Widenhouse | A61P 43/00 |
| 10,136,890 B2 | 11/2018 | Shelton, IV et al. | |
| 10,136,891 B2* | 11/2018 | Shelton, IV | A61L 24/0031 |
| 10,166,023 B2 | 1/2019 | Vendely et al. | |
| 10,172,611 B2 | 1/2019 | Shelton, IV et al. | |
| 10,172,617 B2 | 1/2019 | Shelton, IV et al. | |
| 10,172,618 B2 | 1/2019 | Shelton, IV et al. | |
| 10,251,649 B2 | 4/2019 | Schellin et al. | |
| 10,258,332 B2 | 4/2019 | Schmid et al. | |
| 10,265,091 B2* | 4/2019 | Nativ | A61B 17/32 |
| 10,285,692 B2* | 5/2019 | Widenhouse | A61L 31/10 |
| 10,314,588 B2* | 6/2019 | Turner | A61B 17/068 |
| 10,349,939 B2* | 7/2019 | Shelton, IV | A61B 17/105 |
| 10,368,869 B2 | 8/2019 | Olson et al. | |
| 10,433,846 B2 | 10/2019 | Vendely et al. | |
| 10,517,592 B2 | 12/2019 | Shelton, IV et al. | |
| 10,548,593 B2 | 2/2020 | Shelton, IV et al. | |
| 10,568,621 B2 | 2/2020 | Shelton, IV et al. | |
| 10,569,071 B2* | 2/2020 | Harris | A61B 17/07292 |
| 10,588,623 B2 | 3/2020 | Schmid et al. | |
| 10,772,732 B1 | 9/2020 | Miller et al. | |
| 10,939,911 B2 | 3/2021 | Huitema et al. | |
| 11,116,505 B2 | 9/2021 | Vendely et al. | |
| 11,224,423 B2 | 1/2022 | Shelton, IV et al. | |
| 11,291,449 B2 | 4/2022 | Swensgard et al. | |
| 11,406,377 B2 | 8/2022 | Schmid et al. | |
| 11,504,125 B2 | 11/2022 | Shelton, IV et al. | |
| 11,602,341 B2 | 3/2023 | Shelton, IV et al. | |
| 11,627,961 B2 | 4/2023 | Shelton, IV et al. | |
| 11,707,278 B2* | 7/2023 | Vadali | A61B 17/07207 |
| | | | 227/180.1 |
| 2002/0014951 A1 | 2/2002 | Kramer et al. | |
| 2004/0101546 A1 | 5/2004 | Gorman et al. | |
| 2004/0101548 A1 | 5/2004 | Pendharkar | |
| 2005/0070929 A1 | 3/2005 | Dalessandro et al. | |
| 2007/0021760 A1 | 1/2007 | Kelleher | |
| 2007/0034669 A1 | 2/2007 | De et al. | |
| 2007/0179528 A1* | 8/2007 | Soltz | A61B 17/07292 |
| | | | 227/175.1 |
| 2007/0251835 A1 | 11/2007 | Mika et al. | |
| 2008/0051866 A1 | 2/2008 | Chen et al. | |
| 2009/0093550 A1 | 4/2009 | Rolfes et al. | |
| 2009/0123517 A1 | 5/2009 | Flanagan et al. | |
| 2009/0206142 A1 | 8/2009 | Huitema et al. | |
| 2009/0209031 A1 | 8/2009 | Stopek | |
| 2010/0331880 A1 | 12/2010 | Stopek | |
| 2012/0100200 A1 | 4/2012 | Belcheva et al. | |
| 2012/0241491 A1* | 9/2012 | Aldridge | A61B 17/1155 |
| | | | 227/175.1 |
| 2012/0241498 A1 | 9/2012 | Gonzalez et al. | |
| 2012/0289979 A1 | 11/2012 | Eskaros et al. | |
| 2013/0146643 A1 | 6/2013 | Schmid et al. | |
| 2013/0172929 A1 | 7/2013 | Hess et al. | |
| 2013/0209659 A1 | 8/2013 | Racenet et al. | |
| 2013/0221065 A1 | 8/2013 | Aronhalt et al. | |
| 2013/0256377 A1 | 10/2013 | Schmid et al. | |
| 2014/0155916 A1 | 6/2014 | Hodgkinson et al. | |
| 2014/0166726 A1 | 6/2014 | Schellin et al. | |
| 2014/0205637 A1 | 7/2014 | Widenhouse et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0136831 A1 | 5/2015 | Baxter, III et al. | |
| 2015/0196296 A1 | 7/2015 | Swayze et al. | |
| 2015/0238191 A1 | 8/2015 | Schellin et al. | |
| 2015/0297236 A1 | 10/2015 | Harris et al. | |
| 2015/0351761 A1* | 12/2015 | Shelton, IV | A61B 17/064 |
| | | | 606/219 |
| 2015/0351764 A1 | 12/2015 | Shelton, IV | |
| 2016/0100839 A1 | 4/2016 | Marczyk et al. | |
| 2016/0106427 A1 | 4/2016 | Shelton, IV et al. | |
| 2016/0345976 A1 | 12/2016 | Gonzalez et al. | |
| 2017/0049448 A1* | 2/2017 | Widenhouse | A61B 17/068 |
| 2017/0055992 A1* | 3/2017 | Widenhouse | A61B 17/1155 |
| 2017/0055994 A1 | 3/2017 | Vendely et al. | |
| 2017/0056018 A1* | 3/2017 | Zeiner | A61B 17/32 |
| 2017/0056567 A1 | 3/2017 | Harris et al. | |
| 2017/0119391 A1 | 5/2017 | Schellin et al. | |
| 2017/0281181 A1 | 10/2017 | Matonick et al. | |
| 2017/0296213 A1 | 10/2017 | Swensgard et al. | |
| 2018/0085124 A1 | 3/2018 | Nativ et al. | |
| 2018/0235613 A1 | 8/2018 | Shelton, IV et al. | |
| 2018/0235616 A1* | 8/2018 | Shelton, IV | A61B 17/07292 |
| 2018/0235625 A1 | 8/2018 | Shelton, IV et al. | |
| 2018/0353174 A1 | 12/2018 | Widenhouse et al. | |
| 2018/0353175 A1 | 12/2018 | Widenhouse et al. | |
| 2018/0353659 A1 | 12/2018 | Widenhouse et al. | |
| 2019/0200844 A1 | 7/2019 | Shelton, IV et al. | |
| 2019/0200981 A1 | 7/2019 | Harris et al. | |
| 2019/0201140 A1 | 7/2019 | Yates et al. | |
| 2019/0206004 A1 | 7/2019 | Shelton, IV et al. | |
| 2019/0206562 A1 | 7/2019 | Shelton, IV et al. | |
| 2019/0254655 A1 | 8/2019 | Shelton, IV et al. | |
| 2019/0254656 A1* | 8/2019 | Shelton, IV | A61L 31/041 |
| 2019/0254661 A1* | 8/2019 | Shelton, IV | A61L 31/148 |
| 2019/0328390 A1 | 10/2019 | Harris et al. | |
| 2019/0344064 A1 | 11/2019 | Buchanan | |
| 2020/0205825 A1 | 7/2020 | Vendely et al. | |
| 2020/0238244 A1 | 7/2020 | Tchakalova et al. | |
| 2021/0077094 A1 | 3/2021 | Harris et al. | |
| 2021/0077109 A1 | 3/2021 | Harris et al. | |
| 2021/0346015 A1 | 11/2021 | Krulevitch et al. | |
| 2022/0313145 A1 | 10/2022 | Shelton, IV et al. | |
| 2022/0313245 A1 | 10/2022 | Shelton, IV et al. | |
| 2022/0313246 A1 | 10/2022 | Shelton, IV et al. | |
| 2022/0313247 A1 | 10/2022 | Shelton, IV et al. | |
| 2022/0313248 A1 | 10/2022 | Shelton, IV et al. | |
| 2022/0313255 A1 | 10/2022 | Shelton, IV et al. | |
| 2022/0313256 A1 | 10/2022 | Shelton, IV et al. | |
| 2022/0313258 A1 | 10/2022 | Shelton, IV et al. | |
| 2022/0313259 A1 | 10/2022 | Shelton, IV et al. | |
| 2022/0313260 A1 | 10/2022 | Shelton, IV et al. | |
| 2022/0313262 A1 | 10/2022 | Shelton, IV et al. | |
| 2022/0313874 A1 | 10/2022 | Shelton, IV et al. | |
| 2023/0158214 A1 | 5/2023 | Shelton, IV et al. | |

FOREIGN PATENT DOCUMENTS

| | | |
|---|---|---|
| EP | 2395333 A1 | 12/2011 |
| EP | 2604196 A2 | 6/2013 |
| EP | 2628491 A2 | 8/2013 |
| EP | 3530199 A2 | 8/2019 |
| EP | 3756612 A2 | 12/2020 |
| EP | 3782558 A1 | 2/2021 |
| EP | 3791804 A2 | 3/2021 |
| EP | 3791809 A1 | 3/2021 |
| WO | 9824048 A1 | 6/1998 |
| WO | 2006068999 A2 | 6/2006 |
| WO | 2015187793 A1 | 12/2015 |
| WO | 2020021433 A1 | 1/2020 |
| WO | 2022079516 A1 | 4/2022 |

(56) References Cited

OTHER PUBLICATIONS

U.S. Appl. No. 17/022,520 entitled "Method of Applying Buttress to End Effector of Surgical Stapler", filed on Sep. 16, 2020, 226 pages.
U.S. Appl. No. 17/068,857 entitled "Adaptive Responses From Smart Packaging of Drug Delivery Absorbable Adjuncts", filed on Oct. 13, 2020, 97 pages.
Agren et al. (Jul. 2006) "Action of Matrix Metalloproteinases at Restricted Sites in Colon Anastomosis Repair: An Immunohistochemical and Biochemical Study", Surgery, 140(1):72-82.
Aslanian et al. (Mar.-Apr. 1984) "Dietary Intake and Urinary Excretion of Various Mineral Substances in Patients with Hypertension and Ischemic Heart Disease", Vopr Pitan, (2):16-9(English Abstract).
Bezwada Rao S. (2008) "Controlled Release of Drugs from Novel Absorbable Oligomers and Polymers", White Paper, Bezwada Biomedical, 7 pages.
Bezwada Rao S. (2008) "Functionalized Triclosan for Controlled Release Applications", White Paper, AP Bezwada Biomedical, 6 pages.
Bezwada Rao S. (2010) "Nitric Oxide and Drug Releasing Hydrolysable Macromers, Oligomers and Polymers", Chapter 11 of Biomaterials, ACS Symposium Series, American Chemical Society: Washington, DC, 24 pages.
Bezwada Rao S. (Mar. 2009) "Nitric Oxide and Drug Releasing Hydrolysable Macromers, Oligomers and Polymers", White Paper, Bezwada Biomedical, 9 pages.
Bosmans et al. (2015) "Colorectal Anastomotic Healing: Why the Biological Processes that Lead to Anastomotic Leakage Should Be Revealed Prior to Conducting Intervention Studies", BMC Gastroenterology, 15:180(6 pages).
Broughton et al. (Jun. 2006) "The Basic Science of Wound Healing", Plastic and Reconstructive Surgery, 117(7 Suppl):12S-34S.
Casalani et al. (Oct. 11, 2019) "A Perspective on Polylactic Acid-Based Polymers Use for Nanoparticles Synthesis and Applications", Frontiers in Bioengineering and Biotechnology, 7(259):1-16.
De Hingh et al. (Jun. 21, 2002) "The Matrix Metalloproteinase Inhibitor BB-94 Improves the Strength of Intestinal Anastomoses in the Rat", International Journal of Colorectal Disease, 17(5):348-354.
Fatouros et al. (Oct. 1999) "Influence of Growth Factors Erythropoietin and Granulocyte Macrophage Colony Stimulating Factor on Mechanical Strength and Healing of Colonic Anastomoses in Rats", The European Journal of Surgery, 165(10):986-992.
Gibson et al. (Nov. 2009) "MMPs Made Easy", Wounds International, 1(1):1-6.
Hayden et al. (Jun. 15, 2011) "The Role of Matrix Metalloproteinases in Intestinal Epithelial Wound Healing During Normal and Inflammatory States", Journal of Surgical Research, 168(2):315-324.
Holte et al. (Jun. 2009) "Cyclo-oxygenase 2 Inhibitors and the Risk of Anastomotic Leakage After Fast-Track Colonic Surgery", British Journal of Surgery, 96(6):650-654.
Kaemmer et al. (Oct. 2010) "Erythropoietin (EPO) Influences Colonic Anastomotic Healing in a Rat Model by Modulating Collagen Metabolism", Journal of Surgical Research, 163(2):e67-e72.
Kiyama et al. (Sep. 2002) "Tacrolimus Enhances Colon Anastomotic Healing in Rats", Wound Repair and Regeneration, 10(5):308-313.
Klein et al. (Jan. 2011) "Effect of Diclofenac on Cyclooxygenase-2 Levels and Early Breaking Strength of Experimental Colonic Anastomoses and Skin Incisions", European Surgical Research, 46(1):26-31.
Klein et al. (Jul. 18, 2010) "Physiology and Pathophysiology of Matrix Metalloproteases", Amino Acids, 41(2):271-290.
Krarup et al. (Apr. 26, 2013) "Expression and Inhibition of Matrix Metalloproteinase (MMP)-8, MMP-9 and MMP-12 in Early Colonic Anastomotic Repair", International Journal of Colorectal Disease, 28(8):1151-1159.
Martens et al. (Dec. 1991) "Postoperative changes in collagen synthesis in intestinal anastomoses of the rat: differences between small and large bowel", Gut, 32(12):1482-1487.
Moran et al. (May 15, 2007) "The Effect of Erythropoietin on Healing of Obstructive vs Nonobstructive Left Colonic Anastomosis: An Experimental Study", World Journal of Emergency Surgery, 2:13(6 pages).
Munireddy et al. (Dec. 2010) "Intra-abdominal Healing: Gastrointestinal Tract and Adhesions", Surgical Clinics of North America, 90(6):1227-1236(10 pages).
Øines et al. (Sep. 21, 2014) "Pharmacological Interventions for Improved Colonic Anastomotic Healing: A Meta-Analysis", World Journal of Gastroenterology, 20(35):12637-12648.
Raptis et al. (Mar. 2012) "The Effects of Tacrolimus on Colonic Anastomotic Healing in Rats", International Journal of Colorectal Disease, 27(3):299-308.
Savage et al. (Aug. 1997) "Role of Matrix Metalloproteinases in Healing of Colonic Anastomosis", Diseases of the Colon & Rectum, 40(8):962-970.
Siemonsma et al. (Mar. 1, 2003) "Doxycycline Improves Wound Strength After Intestinal Anastomosis in the Rat", Surgery, 133(3):268-276.
Thompson et al. (2006) "Clinical Review: Healing in Gastrointestinal Anastomoses, Part I", Microsurgery, 26(3):131-136.
Vandenbroucke et al. (Dec. 2014) "Is There New Hope for Therapeutic Matrix Metalloproteinase Inhibition?", Nature Reviews Drug Discovery, 13(12):904-927.
Witte et al. (Aug. 2003) "Repair of Full-thickness Bowel Injury", Critical Care Medicine, 31(8 Suppl):S538-S546.
International Search Report and Written Opinion For Patent Application No. PCT/IB2022/052795, dated Oct. 10, 2022, 17 Pages.
International Search Report and Written Opinion received for Application No. PCT/IB2022/052796, dated Oct. 11, 2022, 18 Pages.
International Search Report and Written Opinion received for Application No. PCT/IB2022/052822, dated Oct. 13, 2022, 18 Pages.
International Search Report and Written Opinion received for PCT Application No. PCT/IB2022/052798, dated Aug. 18, 2022, 14 Pages.
International Search Report and Written Opinion received for PCT Application No. PCT/IB2022/052804, dated Jul. 8, 2022, 16 Pages.
International Search Report and Written Opinion received for PCT Application No. PCT/IB2022/052806, dated Jul. 27, 2022, 17 Pages.
International Search Report and Written Opinion received for PCT Application No. PCT/IB2022/052807, dated Jul. 7, 2022, 14 Pages.
International Search Report and Written Opinion received for PCT Application No. PCT/IB2022/052809, dated Jul. 27, 2022, 17 Pages.
International Search Report and Written Opinion received for PCT Application No. PCT/IB2022/052811, dated Jul. 7, 2022, 18 Pages.
International Search Report and Written Opinion received for PCT Application No. PCT/IB2022/052813, dated Jul. 27, 2022, 15 Pages.
International Search Report and Written Opinion received for PCT Application No. PCT/IB2022/052815, dated Jul. 20, 2022, 13 Pages.
International Search Report and Written Opinion received for PCT Application No. PCT/IB2022/052816, dated Jul. 12, 2022, 16 Pages.
International Search Report and Written Opinion received for PCT Application No. PCT/IB2022/052818, dated Aug. 10, 2022, 14 Pages.
Invitation to Pay Additional Fees received for PCT Application No. PCT/IB2022/052795, dated Jul. 20, 2022, 11 Pages.
Invitation to Pay Additional Fees received for PCT Application No. PCT/IB2022/052796, dated Jul. 27, 2022, 13 Pages.
Invitation to Pay Additional Fees received for PCT Application No. PCT/IB2022/052822, dated Aug. 12, 2022, 13 Pages.
(Mar. 24, 2022) What are Stents?, NIH National Heart, Lung, and Blood Institute, 3 Pages.

(56) References Cited

OTHER PUBLICATIONS

Maurus et al. (2004) "Bioabsorbable Implant Material Review", Operative Techniques in Sports Medicine, 12:158-160.
U.S. Appl. No. 17/217,252, filed Mar. 30, 2021, Method for Treating Tissue.
U.S. Appl. No. 17/216,978, filed Mar. 30, 2021, Compressible Adjuncts With Drug Release Features.
U.S. Appl. No. 17/216,982, filed Mar. 30, 2021, Compressible Adjuncts With Drug Release Features.
U.S. Appl. No. 17/216,985, filed Mar. 30, 2021, Compressible Adjuncts With Drug Dosage Control Features.
U.S. Appl. No. 17/216,994, filed Mar. 30, 2021, Compressible Adjuncts With Different Behavioral Zones.
U.S. Appl. No. 17/216,914, filed Mar. 30, 2021, Smart Packaging for Tissue Adjuncts.
U.S. Appl. No. 17/216,946, filed Mar. 30, 2021, Passively Powered Packaging for Tissue Adjuncts.
U.S. Appl. No. 17/216,953, filed Mar. 30, 2021, Using Smart Packaging in Adjusting Use of Tissue Adjuncts.
U.S. Appl. No. 17/216,960, filed Mar. 30, 2021, Monitoring Healing After Tissue Adjunct Implantation.
U.S. Appl. No. 17/217,578, filed Mar. 30, 2021, Implantable Adjuncts Having Adjustable Degradation Profile.
U.S. Appl. No. 17/217,680, filed Mar. 30, 2021, Compressible Adjuncts With Healing-Dependent Degradation Profile.
U.S. Appl. No. 17/217,736, filed Mar. 30, 2021, Tissue Thickness Compensating Adjuncts Having Regions of Differential Expansion.
U.S. Appl. No. 17/217,784, filed Mar. 30, 2021, Composite Adjuncts That Degrade Through Multiple Different Mechanisms.

\* cited by examiner

COMPRESSIBLE ADJUNCTS WITH FLUID CONTROL FEATURES

FIELD OF THE INVENTION

The present disclosure relates generally to compressible adjuncts and methods of using compressible adjuncts.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling.

Various implantable materials have been developed for use in combination with stapling tissue, however there remains a need for improved materials that address some of the aforementioned problems.

SUMMARY

Compressible adjuncts for use with a surgical cartridge are provided. In one exemplary embodiment, a compressible adjunct includes a biocompatible adjunct material that is configured to be releasably retained on at least one of a staple cartridge and an anvil and that is configured to be delivered to tissue by deployment of staples in the cartridge. The adjunct material includes a lattice main structure having at least one absorbable sub-structure formed in the lattice main structure, the at least one absorbable sub-structure configured to control fluid movement through the adjunct material such that the fluid movement impacts healing of tissue adjacent the adjunct material when the adjunct material is in a tissue deployed state.

The at least one absorbable sub-structure can have a variety of configurations. In some embodiments, the at least one absorbable sub-structure can include at least one of an active flow control structure and a passive flow control structure. In certain embodiments, the at least one absorbable sub-structure can include at least one of a duck bill valve, a flapper valve, and micro-passageways formed in a sidewall of the lattice main structure. In other embodiments, the at least one absorbable sub-structure includes at least one movable valve. The movable valve can be configured to control fluid movement therethrough. In some embodiments, the at least one absorbable sub-structure includes a plurality of absorbable sub-structures that together control a direction of fluid movement through the adjunct material.

The lattice main structure can have a variety of configurations. In some embodiments, the lattice main structure can include a plurality of hollow struts. In such embodiments, the at least one absorbable sub-structure can be formed in at least one of the hollow struts for controlling fluid flow therethrough.

In other embodiments, the lattice main structure can include a plurality of unit cells having passageways therethrough. In such embodiments, the at least one absorbable sub-structure can include at least one microstructure formed in at least one unit cell of the plurality of unit cells for controlling fluid flow through the respective passageway.

The unit cells can have a variety of configurations. In some embodiments, the plurality of unit cells can include at least one Schwarz-P structure. In certain embodiments, at least a portion of the plurality of unit cells can be configured to deform when the adjunct material is compressed so as to draw fluid into the adjunct material when the adjunct material is in a tissue deployed state, pump fluid out of the adjunct material to tissue adjacent the adjunct material when the adjunct material is in a tissue deployed state, or a combination thereof.

In some embodiments, the plurality of unit cells each include at least one internal stopping element. The at least one internal stopping element can be configured to limit the amount of deformation of the respective unit cell when the adjunct material is being compressed.

In another embodiment, a compressible adjunct for use with a surgical cartridge includes a biocompatible adjunct material that is configured to be releasably retained on at least one of a staple cartridge and an anvil and that is configured to be delivered to tissue by deployment of staples in the cartridge. The adjunct material includes at least one drug disposed therein, an intended cut line that extends along a longitudinal axis extending from a first end to a second end of the adjunct material, a retaining segment on a first side of the intended cut line, and a removing segment on a second side of the intended cut line. The adjunct material has a geometry that is configured to locally deliver or store the at least one drug relative to the intended cut line or relative to the retaining and removing segments such that the adjunct material has an asymmetric drug delivery profile of the at least one drug in at least one predetermined direction when the adjunct material is in a tissue deployed state.

In some embodiments, the compressible adjunct can include an indicator feature. The indicator feature can be configured to indicate at least one of the removing segment of the adjunct material and a location of the at least one drug within the adjunct material.

In some embodiments, the at least one drug can be only disposed within the retaining segment of the adjunct material.

The adjunct material can have a variety of configurations. In some embodiments, the adjunct material can have a tissue-contacting surface and a cartridge-contacting surface that is opposite the tissue-contacting surface. The tissue-contacting surface can differ from the cartridge-contacting surface in at least one of concentration and type of the at least one drug.

Stapling assemblies for use with a surgical stapler are also provided. In one exemplary embodiment, a stapling assembly includes a cartridge and a biocompatible adjunct. The cartridge has a plurality of staples disposed therein, in which the plurality of staples are arranged in staple rows and configured to be deployed into tissue. The biocompatible adjunct is configured to be releasably retained on the cartridge and is configured to be delivered to tissue by deployment of the plurality of staples. The adjunct includes a lattice macrostructure having a plurality of absorbable microstructures formed therein, in which each absorbable microstructure is configured to direct, limit, or prevent fluid movement as fluid flows through the lattice macrostructure.

The plurality of absorbable microstructures can have a variety of configurations. In some embodiments, the plurality of absorbable microstructures can include at least one of an active flow control structure and a passive flow control structure. In other embodiments, the plurality of absorbable microstructures can include movable valves.

The lattice macrostructure can have a variety of configurations. For example, in some embodiments, the lattice macrostructure can include a plurality of Schwarz-P structures having passageways therethrough. The plurality of absorbable microstructures can include at least one microfeature that formed in at least one Schwarz-P structure of the plurality of Schwarz-P structures for controlling fluid flow through the respective passageway. In certain embodiments, at least a portion of the plurality of Schwarz-P structures can be configured to deform when the adjunct is compressed so as to draw fluid into the adjunct when the adjunct is in a tissue deployed state, pump fluid out of the adjunct to tissue adjacent the adjunct when the adjunct is in a tissue deployed state, or a combination thereof. In such embodiments, at least a portion of the plurality of Schwarz-P structures can be positioned within regions of the adjunct that do not overlap with the staple rows when the adjunct is releasably retained on the cartridge.

BRIEF DESCRIPTION OF THE DRAWINGS

This invention will be more fully understood from the following detailed description taken in conjunction with the accompanying drawings, in which.

DETAILED DESCRIPTION

Figure 1:
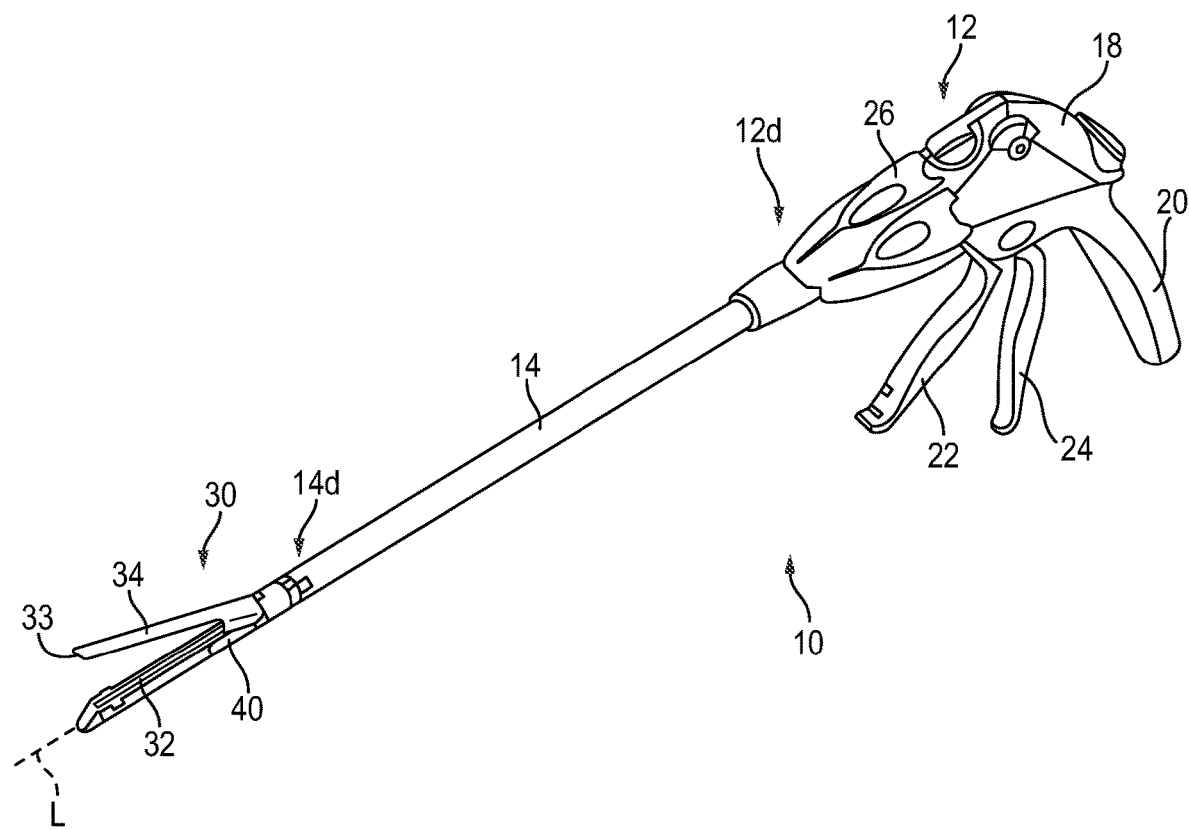
FIG. 1 is a perspective view of one exemplary embodiment of a conventional surgical stapling and severing instrument.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, referred to herein as "adjuncts," in conjunction with surgical instruments to help improve surgical procedures. "Adjuncts" are also referred to herein as "adjunct materials." While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing, and/or is experiencing another tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissue's movement around these puncture sites can minimize the size the holes may grow to under tension. In some instances, the adjunct(s) can be configured to wick or absorb beneficial fluids, e.g., sealants, blood, glues, and the like, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts.

In other embodiments, the adjunct(s) can be used with surgical instruments that are configured to seal tissue without using staples (e.g., by using energy, such as RF or ultrasound), for example, as described in U.S. Pat. No. 10,172,611, which is incorporated by reference herein in its entirety.

In some instances, the adjunct(s) can be configured to compensate for variations in tissue thickness when the adjunct(s) are stapled to tissue. In such instances, the adjunct can be also be referred to as a "tissue thickness compensator." A tissue thickness compensator has an uncompressed (undeformed), or pre-deployed, height that is greater than the height of a staple that is in a formed configuration. Additional details on exemplary tissue thickness compensators can be found in, for example, U.S. Pat. No. 8,864,007, which is incorporated by reference herein in its entirety. A tissue thickness compensator can be attached and released from a staple cartridge in a variety of ways, for example, as described in U.S. Pat. Nos. 9,272,406, and 10,136,890, each of which is incorporated by reference herein in its entirety.

In addition to the disclosures herein, additional details pertaining to the adjunct(s) and other exemplary adjuncts can be found in, for example, U.S. Pat. Nos. 10,172,611 and 10,433,846 and U.S. patent application Ser. No. 17/009,769, filed on Sep. 1, 2020, and entitled "Compressible Non-Fibrous Adjuncts," each of which is incorporated herein by reference in its entirety.

Alternatively or in addition, the adjunct(s) can be configured to promote tissue ingrowth. In various instances, it is desirable to promote the ingrowth of tissue into an implantable adjunct, to promote the healing of the treated tissue (e.g., stapled and/or incised tissue), and/or to accelerate the patient's recovery. More specifically, the ingrowth of tissue into an implantable adjunct may reduce the incidence, extent, and/or duration of inflammation at the surgical site. Tissue ingrowth into and/or around the implantable adjunct may, for example, manage the spread of infections at the surgical site. The ingrowth of blood vessels, especially white blood cells, for example, into and/or around the implantable adjunct may fight infections in and/or around the implantable adjunct and the adjacent tissue. Tissue ingrowth may also encourage the acceptance of foreign matter (e.g., the implantable adjunct and the staples) by the patient's body and may reduce the likelihood of the patient's body rejecting the foreign matter. Rejection of foreign matter may cause infection and/or inflammation at the surgical site.

Alternatively or in addition, the adjunct(s) can have medicant(s) thereon and/or therein. The medicant(s) can vary depending on the desired effect of the medicant(s) on the surrounding tissue. As a non-limiting example, medicant(s) can be provided to influence hemostasis, inflammation, macrophages, and/or fibroblasts. Medicant(s) can be mixed or combined in any combination or a medicant can be provided alone, again depending on the desired effect on the tissue. The medicant(s) can be eluted from the adjunct(s) in a variety of different ways. As non-limiting examples, coatings on the adjunct(s) can be varied to be absorbed at different times, thereby releasing the medicant(s) at different times; the adjunct(s) can be varied to allow diffusion of the medicant(s) across the adjunct(s) at varying rates; the adjunct(s) can vary in molecular weight and/or physical characteristics to cause release of the medicant(s) at different times; etc. In addition to the disclosures herein, additional details on drug eluting adjuncts can be found in U.S. Pat. Nos. 9,232,941 and 10,569,071, each of which is incorporated herein by reference in its entirety.

Surgical Stapling Instruments

A variety of surgical instruments can be used in conjunction with the adjunct(s) and/or medicant(s) disclosed herein. The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of different surgical procedures on a variety of tissues in a variety of different surgical procedures, for example in thoracic surgery or in gastric surgery.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. The lower jaw 32 has a staple channel 56 configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 or other cutting element can be associated with the firing system to cut tissue during the stapling procedure.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent a distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

Figure 2:
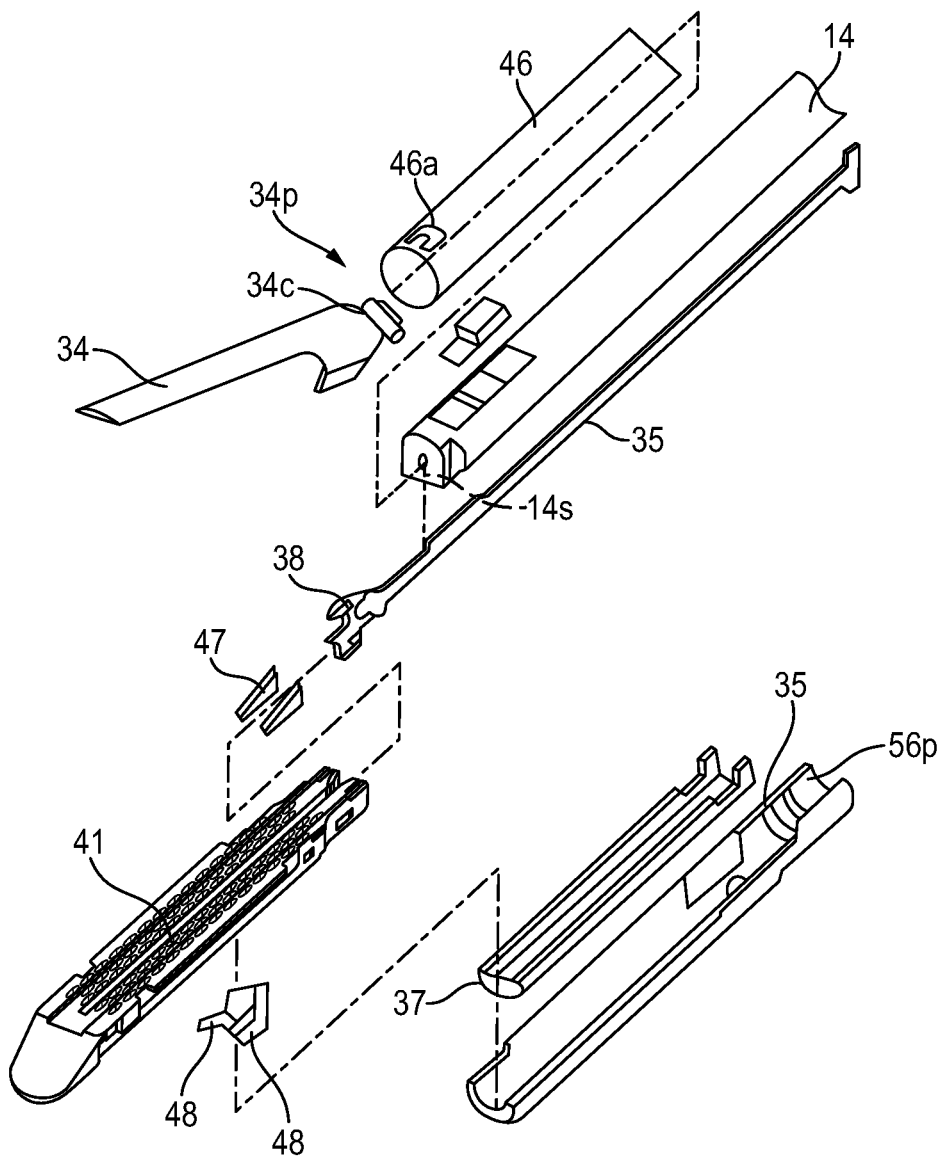
FIG. 2 is a top view of a staple cartridge for use with the surgical stapling and severing instrument of FIG. 1.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
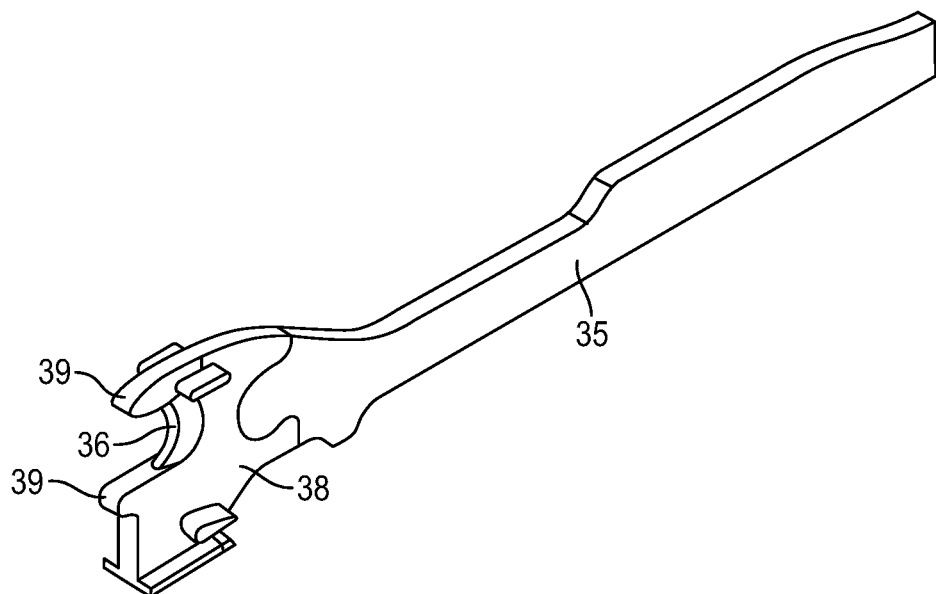
FIG. 3 is a perspective view of a firing bar of the surgical stapler of FIG. 1, the firing bar having an E-beam at a distal end thereof.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47 shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
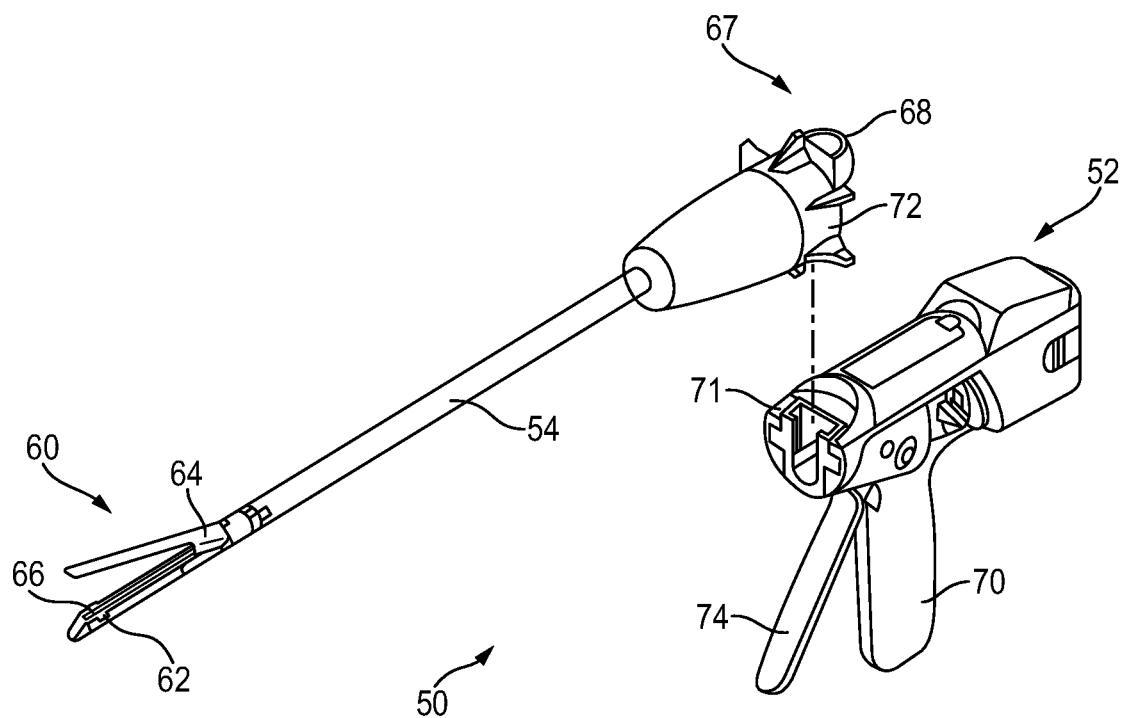
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 64 can move to the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
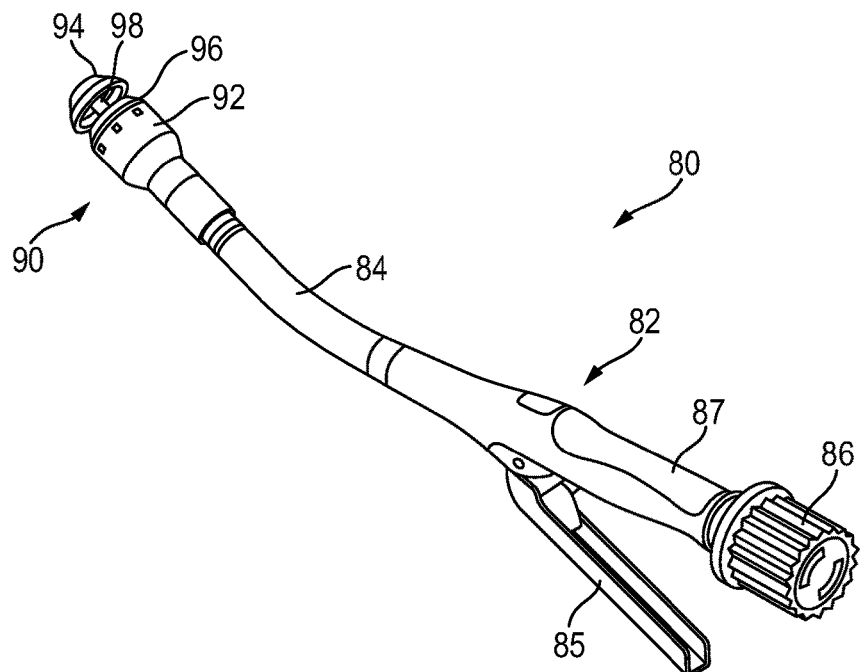
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft can be disposed within the cartridge assembly 92 and extend distally outside of the cartridge assembly 92, terminating in a distal mating feature. The second portion of the shaft can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, e.g., move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, and 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, and U.S. patent application Ser. No. 14/300,954, entitled "Adjunct Materials and Methods of Using Same in Surgical Methods for Tissue Sealing," and filed on Jun. 10, 2014, which are hereby incorporated by reference herein in their entireties.

Implantable Adjuncts

Figure 6:
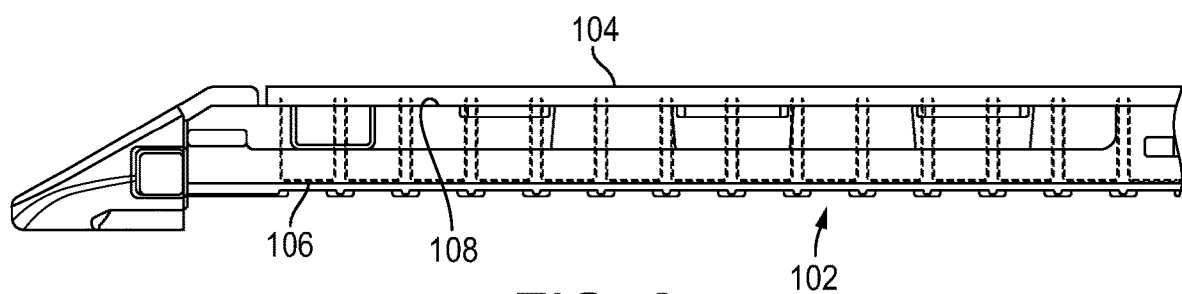
FIG. 6 is a longitudinal cross-sectional view of an exemplary embodiment of a staple cartridge having an exemplary adjunct attached to a top or deck surface thereof.

As indicated above, various implantable adjuncts are provided for use in conjunction with surgical stapling instruments. When used in conjunction with a surgical stapler, the adjunct(s) can be disposed between and/or on jaws of the stapler, incorporated into a staple cartridge disposed in the jaws, or otherwise placed in proximity to the staples. For example, as shown in FIG. 6, an adjunct 104 is positioned against a staple cartridge 102. For sake of simplicity, the adjunct 104 is generally illustrated in FIG. 6, and various structural configurations of the adjunct are described in more detail below. While partially obstructed in FIG. 6, the staple cartridge 102 includes staples 106 that are configured to be deployed into tissue. The staples 106 can have any suitable unformed (pre-deployed) height. For example, the staples 106 can have an unformed height between about 2 mm and 4.8 mm. Prior to deployment, the crowns of the staples can be supported by staple drivers (not shown).

In the illustrated embodiment, the adjunct 104 can be releasably mated to at least a portion of the top surface or deck surface 108 of the staple cartridge 102. In some embodiments, the top surface 108 of the staple cartridge 102 can include one or more surface features. Alternatively, or in addition, one or more adhesives can be used to releasably mate the adjunct to the staple cartridge 102. The one or more surface features and/or the one or more adhesives can be configured to engage the adjunct 104 to avoid undesirable movements of the adjunct 104 relative to the staple cartridge 102 and/or to prevent premature release of the adjunct 104 from the staple cartridge 102. Exemplary surface features are described in U.S. Patent Publication No. 2016/0106427, which is incorporated by reference herein in its entirety. Additional details on adhesives for temporary attachment to instruments and other exemplary adhesives can be found in U.S. Pat. Nos. 9,282,962, 10,172,617, 10,172,618, 10,258,332, 10,517,592, 10,548,593, 10,568,621, and 10,588,623, each of which is incorporated by reference herein in its entirety. Additional details on attachment methods and other exemplary methods can be found in U.S. Pat. Nos. 10,166,023 and 10,349,939 and U.S. patent application Ser. No. 17/022,520, filed on Sep. 16, 2020, and entitled "Method of Applying Buttress to End Effector of Surgical Stapler," each of which is incorporated by reference herein in its entirety.

Figure 7:
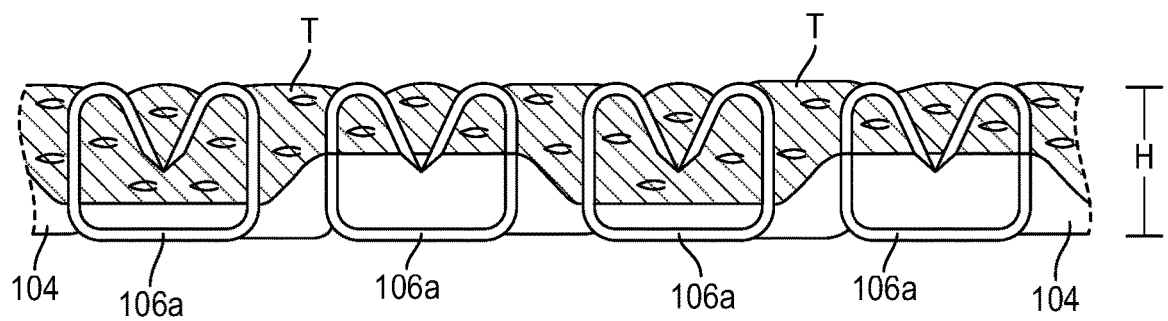
FIG. 7 is a partial-schematic illustrating the adjunct of FIG. 6 in a tissue deployed condition.

In certain instances, the adjunct can be compressible to permit the adjunct to compress to varying heights to thereby compensate for different tissue thickness that are captured within a deployed staple. For example, as illustrated in FIG. 6, the adjunct 104 has an uncompressed (undeformed), or pre-deployed, height and is configured to deform to one of a plurality of compressed (deformed), or deployed, heights. As such, the adjunct 104 can have an uncompressed height which is greater than the fired height of the staples 106 disposed within the staple cartridge 102 (e.g., the height (H) of the fired staple 106*a* in FIG. 7). That is, the adjunct 104 can have an undeformed state in which a maximum height of the adjunct 104 is greater than a maximum height of a fired staple (e.g., a staple that is in a formed configuration). In such instances, the adjunct can be referred to as a "tissue thickness compensator." In one embodiment, the uncompressed height of the adjunct 104 can be about 10% taller, about 20% taller, about 30% taller, about 40% taller, about 50% taller, about 60% taller, about 70% taller, about 80% taller, about 90% taller, or about 100% taller than the fired height of the staples 106. In certain embodiments, the uncompressed height of the adjunct 104 can be over 100% taller than the fired height of the staples 106, for example.

The adjuncts can have a variety of configurations, and can be formed from various materials. In general, an adjunct can be formed from one or more of a film, a foam, an injection molded thermoplastic, a vacuum thermoformed material, a fibrous structure, an additive manufacturing material, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Examples of various foam adjuncts are further described in previously mentioned U.S. Pat. No. 8,393,514 entitled "Selectively Orientable Implantable Fastener Cartridge" and filed Sep. 30, 2010, which is incorporated by reference herein in its entirety.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways, for example, it can be an extruded or a compression molded film.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

In other embodiments, the adjunct can be formed using a 3D printing process(es) compatible with absorbable polymers. Non-limiting examples of suitable 3D printing processes include stereolithography (SLA or SL), material jetting, selective laser sintering (SLS), and fused filament fabrication as understood by a person skilled in the art.

The adjunct can also be a hybrid construct, such as a laminate composite or melt-locked interconnected fiber. Examples of various hybrid construct adjuncts are further described in U.S. Pat. Pub. No. 2013/0146643 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

Materials

The adjuncts in accordance with the described techniques can be formed from various materials. The materials can be used in various embodiments for different purposes. The materials can be selected in accordance with a desired therapy to be delivered to tissue so as to facilitate tissue in-growth. The materials described below can be used to form an adjunct in any desired combination.

The materials can include bioabsorbable and biocompatible polymers, including homopolymers and copolymers. Non-limiting examples of homopolymers and copolymers include p-dioxanone (PDO or PDS), polyglycolic acid (PGA) (e.g., Dexon and Neoveil), poly(lactic-co-glycolic acid) (PLGA), polycaprolactone (PCL), polyglycolide (PGL), trimethylene carbonate (TMC), polylactic acid (PLA) (e.g., Linvatec Bioscrew and Bionx Implants Smart Screw), poly(trimethylene carbonate (PTMC), polyethylene diglycolate (PEDG), poly(propylene fumarate) (PPF), polyethylene ether (PEE), poly(ethylene glycol) (PEG), poly(N-isopropylacrylamide, poly(amino acid), poly(epoxycarbonate), poly(-oxypropylene carbonate), poly(diol citrates), polymethacrylate anhydrides, poly(ethoxyethylene diglycolate), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides (e.g., REVA ReZolve Stents), and tyrosine-based polyesteramides (e.g., TYRX). The copolymers can also include poly(lactic acid-co-polycaprolactone) (PLA/PCL) (e.g., 16-18 month hydrolyzed), poly(L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), LPLA/DLPLA (e.g., Optima), PLGA-PCL (e.g., 15:85 (PCL: 50% D,L-Lactide: 50% Glycolide), 40:60 (PCL: 50% D,L-Lactide: 50% Glycolide), and 40:60 (PCL: 85% D,L-Lactide: 15% Glycolide), PLGA-PCL-PLGA, and PLGA-PEG-PLGA.

An adjunct can also include special polymer terminations, including (meth)acrylate and organically-derived polymers. Non-limiting examples of organically-derived polymers include those derived from collagen (e.g., Avitene, Endoavitene, Instat, Integran, Veritas, and Microfibrillar Collagen (MFC)).

An adjunct can also include active agents, such as active cell culture (e.g., diced autologous tissue, agents used for stem cell therapy (e.g., Biosutures and Cellerix S.L.), hemostatic agents, and tissue healing agents. Non-limiting examples of hemostatic agents can include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

The adjuncts described herein can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Non-limiting examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Non-limiting examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Non-limiting examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional non-limiting examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-1a, IL-1b, Canakinumab, IL-2, Aldesleukin, Interking, Denileukin Diftitox, IL-3, IL-6, IL-8, IL-10, IL-11, and Oprelvekin). The non-limiting examples of the growth factors further include erythropoietin (e.g., Darbepoetin, Epocept, Dynepo, Epomax, NeoRecormon, Silapo, and Retacrit).

Non-limiting examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Non-limiting examples of anesthetics include local anesthetics (e.g., Lidocaine, Benzocaine, and Ropivacaine) and general anesthetic.

Non-limiting examples of tissue matrix degradation inhibitors that inhibit the action of metalloproteinases (MMPs) and other proteases include MMP inhibitors (e.g., exogenous MMP inhibitors, hydroxamate-based MMP inhibitors, Batimastat (BB-94), Ilomastat (GM6001), Marimastat (BB2516), Thiols, Periostat (Doxycycline), Squaric Acid, BB-1101, Hydroxyureas, Hydrazines, Endogenous, Carbamoylphosphates, Beta Lactams, and tissue Inhibitors of MMPs (TIMPs)).

Non-limiting examples of anti-cancer agents include monclonial antibodies, bevacizumab (Avastin), cellular/chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), *vinca* alkaloids agents that inhibit mitosis and microtubule formation (e.g., Vinblastine, Vincristine, Vindesine, Vinorelbine), angiostatic inhibiting agents that inhibit cell growths or cell expansion (e.g., Axitinib (Inlyta), Bevacizumab (Avastin), Cabozantinib (Cometriq), Everolimus (Afinitor, Zortress) Lenalidomide (Revlimid), Pazopanib (Votrient), Ramucirumab (Cyramza), Regorafenib (Stivarga), Sorafenib (Nexavar), Sunitinib (Sutent), Thalidomide (Synovir, Thalomid), Vandetanib (Caprelsa), Zib-aflibercept (Zaltrap), antiangiogenic polysaccharide, aplidine (dehydrodidemnin B), sapogenins viz. 20(S)-protopanaxadiol, and 20(S)-protopanaxatriol), anti-ileus agents, pro-motility agents, immunosuppresants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and anti-angiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, non-limiting examples of which include Hyaluronic acid/Carboxymethyl cellulose (seprafilm), Oxidized Regenerated Cellulose (Interceed), and Icodextrin 4% (Extraneal, Adept).

Exemplary medicants also include agents that encourage blood supply regeneration following coronary artery disease (CAD) (e.g., $VEGF_{165}$ protein, $AdVEGF_{165}$, $AdVEGF_{121}$, and $VEGF_{165}$ plasmid) or periphery artery disease (PAD) (e.g., $VEGF_{165}$ plasmid, $AdVEGF_{121}$, SB-509 (SFP-VEGF plasmid), $AdVEGF_{165}$, and Ad2-HIF1α-VP16 (WALK trial)).

Drug Release

An adjunct in accordance with the described techniques can be associated with at least one medicant in a number of different ways, so as to provide a desired effect, such as on tissue in-growth, in a desired manner. The at least one medicant can be configured to be released from the adjunct in multiple spatial and temporal patterns to trigger a desired healing process at a treatment site. The medicant can be disposed within, bonded to, incorporated within, dispersed within, or otherwise associated with the adjunct. For example, the adjunct can have one or more regions releasably retaining therein one or more different medicants. The regions can be distinct reservoirs of various sizes and shapes and retaining medicants therein in various ways, or other distinct or continuous regions within the adjuncts. In some aspects, a specific configuration of the adjunct allows it to releasably retain therein a medicant or more than one different medicant.

Regardless of the way in which the medicant is disposed within the adjunct, an effective amount of the at least one medicant can be encapsulated within a vessel, such as a pellet which can be in the form of microcapsules, microbeads, or any other vessel. The vessels can be formed from a bioabsorbable polymer.

Targeted delivery and release of at least one medicant from an adjunct can be accomplished in a number of ways which depend on various factors. In general, the at least one medicant can be released from the adjunct material as a bolus dose such that the medicant is released substantially immediately upon delivery of the adjunct material to tissue. Alternatively, the at least one medicant can be released from the adjunct over a certain duration of time, which can be minutes, hours, days, or more. A rate of the timed release and an amount of the medicant being released can depend on various factors, such as a degradation rate of a region from which the medicant is being released, a degradation rate of one or more coatings or other structures used to retains the medicant within the adjuncts, environmental conditions at a treatment site, and various other factors. In some aspects, when the adjunct has more than one medicant disposed therein, a bolus dose release of a first medicant can regulate a release of a second medicant that commences release after the first medicant is released. The adjunct can include multiple medicants, each of which can affect the release of one or more other medicants in any suitable way.

Release of at least one medicant as a bolus dose or as a timed release can occur or begin either substantially immediately upon delivery of the adjunct material to tissue, or it can be delayed until a predetermined time. The delay can depend on a structure and properties of the adjunct or one or more of its regions.

An adjunct material can be configured to have a structure that facilitates distribution of effective amounts of one or more medicants carried within the adjunct to provide a desired effect. For example, the targeted delivery of the medicants can be accomplished by incorporating the medicants into regions (e.g., reservoirs such as pores or other structures) within the adjunct formed in a pattern that allows a certain spatial distribution of the medicants upon their delivery. The medicants disposed within the reservoir can be incorporated into distinct vessels. A reservoir can include more than one type of different medicants. The one or more medicants can be eluted from the adjunct in a homogeneous manner or in heterogeneous spatial and/or temporal manner to deliver a desired therapy. The structure of the adjunct and the way in which the medicants are released therefrom can be used to influence or control tissue re-growth. Moreover, the tissue regrowth can be encouraged in certain locations at the treatment site and discouraged at other locations at the treatment site.

Fluid Control Features and Drug Release Features

In certain embodiments, the adjuncts can have a variety of configurations that are designed to control fluid movement into, out of, and/or through the adjuncts when the adjuncts are in a tissue deployed state (e.g., stapled to tissue in vivo). This fluid control can encourage the mobility of cells and bi-products into and out of the adjunct during tissue remodeling while the adjunct is in a tissue deployed state. Further, this fluid control can impact the ion level of the tissue that is stapled to the adjunct such that the fluid movement through the adjunct can disrupt or enhance environment effects on tissue remodeling.

The adjuncts can generally be formed from a biocompatible adjunct material that is configured to be releasably retained on a staple cartridge and that is configured to be delivered to tissue by deployment of staples in the cartridge. In an exemplary embodiment, the adjunct material can include a lattice main structure having at least one absorbable sub-structure formed in the lattice main structure. The at least one absorbable sub-structure can be configured to control fluid movement into, out of, and/or through the adjunct material such that the fluid movement impacts healing of tissue adjacent the adjunct material when the adjunct material is in a tissue deployed state. As used herein, the terms "lattice main structure" and "absorbable substructure" are used synonymously with the terms "lattice macrostructure" and "absorbable microstructure," respectively.

In order to enable formation of macro and micro structures, the adjuncts can be non-fibrous adjuncts. Unlike conventional adjuncts (e.g., adjuncts that are not three-dimensionally printed, such as foam adjuncts and woven/non-woven fibrous adjuncts), the non-fibrous adjuncts are three-dimensionally (3D) printed and therefore can be formed with microstructures (units or sub-structures) that are consistent and reproducible. In certain embodiments, however, the non-fibrous adjuncts can include separate fibrous features to help enhance tissue ingrowth within the adjunct.

As described above, the fluid control structures are configured to impact fluid movement into, out of, and/or through the adjunct. Fluid movement can also be used to control drug release from the adjunct (e.g., when the adjunct contains at least one drug disposed therein and is in a tissue deployed state) and/or to control drug flow through the adjunct. For example, in embodiments wherein the adjunct contains at least one drug disposed therein, fluid ingress could control the saturation of the at least one drug and the fluid egress can control the drug dosage being released. As such, controlling the fluid movement (e.g., rate and/or volume) could therefore drive the drug dosage being released from the adjunct. Further, since fluid can serve as the carrier for the at least one drug, directing fluid movement in predetermined direction(s) through the adjunct can be used to define the drug release location(s) of the adjunct. As such, a person skilled in the art will therefore appreciate that any of the fluid control features disclosed herein (e.g., absorbable sub-structures) can be used in combination with drug(s) retained within the adjunct for the transport thereof to tissue adjacent the adjunct when the adjunct is in a tissue deployed state.

In certain embodiments, the at least one absorbable sub-structure can include two or more absorbable sub-structures that together control a direction of fluid movement through the adjunct material. The absorbable sub-structures can have generally uniform configurations (e.g., uniform within manufacturing tolerances) or different configurations. In one embodiment, the absorbable sub-structures include first absorbable sub-structures having a first configuration and second absorbable sub-structures having a second configuration that is different than the first configuration.

The at least one absorbable sub-structure can be an active flow control structure (e.g., a structure that operates in response to an outside energy input to manipulate fluid flow) or a passive flow control structure (e.g., a structure that operates without an outside energy input to manipulate fluid flow). In certain embodiments, the at least one absorbable sub-structure can include first absorbable sub-structures that are active flow control structures and second absorbable sub-structures that are passive flow control structures. Non-limiting examples of active flow control structures include structures that are configured to undergo a deformation upon an applied outside force to the adjunct (e.g., the force being applied by tissue that is stapled to the adjunct) so as to pump fluid out of the adjunct or draw fluid into the adjunct. These structures can include, for example, seals, degradable walls, valves and other features (e.g., unit cells or portions thereof) that change state as the adjunct undergoes shape changes as the adjunct, or portion(s) thereof, is exposed to externally applied force(s). These structures can act as fluid pumps, vacuum chambers, one-way valving, or the like to encourage large boluses of fluid(s) to move dependent on the structure's exposure to outside forces and movements. Non-limiting examples of passive flow control structures include wicking structures, micro-passageways, or other structures that direct fluid through the adjunct without any outside intervention (e.g., in response to a pressure differential within the adjunct). Further, such structures can be used to create continuous directional fluid transport.

The at least one absorbable sub-structure can have a variety of configurations. For example, in some embodiments, the at least one absorbable sub-structure can be designed as a movable valve that is configured to control fluid movement therethrough. Non-limiting examples of a movable valve include a duck bill valve, a flapper valve, and the like. Alternatively, or in addition, the at least one absorbable sub-structure can include micro-passageways formed in a sidewall of the lattice main structure. The micro-passageways can be formed on an interior surface, an exterior surface of the sidewall, or a combination thereof. For example, first micro-passageways can be formed on inner surface of the wall and second micro-passageways can be formed on the outer surface of the sidewall. In certain embodiments, the micro-passageways can be configured to draw fluid therethrough via capillary action.

The fluid direction through the micro-passageways can be controlled or uncontrolled allowing for homogenous or directed flow. In some embodiments, the micro-passageways can include at least one microfeature that is configured to direct fluid in a predefined direction though the respective micro-passageway. For example, the at least one microfeature can include flexible wicking elements that extend from the sidewall of the lattice main structure and into respective micro-passageways. The flexible wicking elements can extend at any suitable angle relative to the sidewall such that the flexible wicking elements can direct fluid through the micro-passageways and thus, through the respective portions of the lattice main structure, in one or more predefined directions. A person skilled in the art will appreciate that the angle(s) at which the flexible wicking elements extend depend at least in part on desired direction of flow through the respective micro-passageway and the structural configuration of the respective sidewall of the lattice main structure.

The lattice main structure can be formed of unit cells. The unit cells can have a variety of configurations. The unit cells can be formed of strut-based unit cells, which are characterized by the presence of sharp corners or angles, or non-strut-based unit cells can be characterized by curved surfaces. In some embodiments, with strut-based unit cells, the unit cells can be formed of hollow struts. For example, the hollow struts can be in the form of hollow tubes, which have higher bending strength that solid tubes of the same mass. Hollow tubes can therefore reduce the total amount of material of the implanted adjunct while also maintaining a high enough compressive strength. Further, in certain embodiments, the hollow tubes can in the form of an "I" shape or any other suitable that can move material away from its neutral axis.

With non-strut based unit cells, the unit cells, for example, can be based on triply periodic minimal surfaces (TPMS). TPMS is a minimal surface that repeats itself in three dimensions. The term "minimal surface" as used in this description refers to a minimal surface as known in mathematics. As such, in some embodiments, the unit cell can be a triply periodic minimal surface structure (e.g., Schwarz-P, Schwarz Diamond, and the like) having passageways extending therethrough. For example, the non-strut based unit cells can be a hollow structure. Additional details on triply periodic minimal surface structures, such as Schwarz-P structures can be found in previously mentioned U.S. patent application Ser. No. 17/009,740, filed Sep. 1, 2020, and entitled "Compressible Non-Fibrous Adjuncts," which is incorporated herein by reference in its entirety. In certain embodiments, the lattice main structure can include a combination of strut-based unit cells (e.g., hollow struts) and non-strut based unit cells (e.g., one or more triply periodic minimal surface structures).

The structural configurations of the unit cells disclosed herein can be tailored to enhance cellular ingrowth within the adjunct. For example, the sizes of the voids or passageways through the unit cells can be tailored to such to a size that has the least impact on cellular mobility therethrough (e.g., about 50 microns to 75 microns). Alternatively, or in addition, the adjunct can be designed with a maximum closed porosity that does not substantially interfere with tissue ingrowth (e.g., tissue granulation or filing, bridging or healing within the open spaces of the adjunct). For example, in some embodiments, the maximum closed porosity of the adjunct can be about 500 microns.

Further, the internal cavities and/or internal surfaces of the unit cells and/or interstitial space between the unit cells can include fibrous features to encourage tissue ingrowth. In some embodiments, fibers can be disposed with the internal cavity of one or more unit cells (e.g., surgical fibrillary can be loosely packed within an internal cavity of a unit cell). Alternatively, or in addition, fibers can be disposed within the interstitial spaces (e.g., concave areas) between the unit cells. Further, alternatively or in addition, fiber-like structures can be printed onto the internal surface(s) of one or more unit cells and/or the internal surface(s) of one or more unit cells can be textured.

The structural configurations of the unit cells disclosed herein can also be tailored to effect variable mechanical responses within the same adjunct, e.g., in the lateral and/or longitudinal directions (e.g., y- and/or z-directions, respectively). For example, an adjunct can be formed of at least two or more different lattice structures, each exhibiting a different compressive behavior. In some embodiments, the perimeter of the adjunct could be more compliant while stiffer regions are located closer to the intended cut line of the adjunct. By way of example, the wall adjacent to the intended cut line itself could be mostly solid or rigid thereby allowing for a more controlled and cleaner cut of the adjunct along the intended cut line. Further, the softer perimeter of the adjunct could protect tissue outside of and adjacent to the jaws (e.g., the jaws of a surgical stapler) from collateral compressive damage.

In some embodiments, the unit cells can be defined by one or more walls, in which some of the walls are hollow (e.g., having void space between opposing exterior surfaces) and others are solid, thereby creating preferential wall bending among the one or more walls. In certain embodiments, any solid wall of the unit cells can include internal voids that create flex zones where the solid wall initially bends prior to the wall bending as a whole (e.g., when a force is applied to the adjunct).

In some embodiments, the one or more walls of the unit cell can be populated with small non-interconnected voids (e.g., in the form of spheres and/or cylinders) that create a substantially incompressible outer shell that is flexible. That is, the small non-interconnected voids would allow the mostly rigid polymer of the one or more walls to be more flexible since these voids could enable bending without direct compressions of the internal aspects of the one or more walls. In such embodiments, the bi-modal nature of the outer shell can be increased such that the unit cell can more easily move between two different states based on a predefined force.

The adjuncts disclosed herein can also include internal and/or external features that promote or inhibit selective deformation of the adjunct (e.g., stretching, bending, compressing, and the like). For example, the adjuncts can include one or more internal stopping elements that are configured to limit the amount of deformation of the adjunct when the adjunct is being compressed. Alternatively, or in addition, the adjunct can include surface features that prevent the adjunct from stretching while releasably retained on a cartridge of a stapling assembly. Alternatively, or in addition, the adjunct can include surface features (e.g., surface friction features) that are configured to minimize slippage of the adjunct relative to a top surface of a staple cartridge when the adjunct is releasably retained thereon and/or relative to tissue when the adjunct is stapled thereto. Additional details on and other exemplary embodiments of internal features and surface features that are suitable to promote or inhibit selective deformation of an adjunct disclosed herein can be found in U.S. patent application Ser. No. 15/901,087, filed on Feb. 21, 2018, and entitled "Three Dimensional Adjuncts," and previously mentioned U.S. patent application Ser. No. 17/009,769, filed on Sep. 1, 2020, and entitled "Compressible Non-Fibrous Adjuncts," each of which is incorporated herein by reference in its entirety.

In certain embodiments, the at least one absorbable sub-structure can include at least one microstructure formed in at least one unit cell for controlling fluid flow through the respective passageway. For example, the at least one microstructure can be a micro-passageway that is formed in the sidewall of the unit cell. The micro-passageway can be in fluid communication with the passageway of the respective unit cell. In other embodiments, the at least one absorbable sub-structure can include other fluid control structures, such as a movable valve (e.g., duck bill valve, a flapper valve, and the like) that is formed in at least one of the unit cells.

In certain embodiments, at least a portion of the unit cells can be configured to deform when the adjunct material is compressed so as to draw fluid into the adjunct material (e.g., when the adjunct material is in a tissue deployed state) and/or to drive fluid out of the adjunct material to tissue adjacent the adjunct material (e.g., when the adjunct material is in a tissue deployed state). As such, this portion of unit cells can serve as pumping elements within the lattice main structure to drive fluid flow through the adjunct material. In such embodiments, this portion of unit cells can be concentrated outside of the staple puncture zones of the adjunct material (e.g., zones or regions of the adjunct material that are configured to overlap with staples disposed in a cartridge that the adjunct material is to be releasably retained thereto).

Further, in some embodiments, lattice main structure can include connecting structures that extend between and connect adjacent unit cells to each other. The connecting structures can be in the form of hollow tubes. As such, the connecting structures can serve as channeling elements within the lattice main structure to direct fluid flow through the adjunct material. Alternatively or in addition, the connecting structures can serve as pumping elements within the lattice main structure.

In some embodiments, the lattice main structure can include hollow struts. In certain embodiments, the at least one absorbable sub-structure can be formed within at least one of the hollow struts for controlling fluid flow therethrough. In one embodiment, the hollow struts are the connecting structures that extend between and connect adjacent unit cells to each other.

Each exemplary adjunct as described below is illustrated in partial form (e.g., not in full-length), and therefore a person skilled in the art will appreciate that the adjunct can be longer in length, e.g., along its longitudinal axis ($L_A$) as identified in each embodiment. The length can vary based on a length of the staple cartridge or anvil. The width can also vary as needed. Further, each exemplary adjunct is configured to be positioned atop a cartridge or anvil surface such that the longitudinal axis L of each adjunct is aligned with and extends along the longitudinal axis ($L_A$) of the cartridge or anvil. These adjuncts are structured so as to compress when exposed to compressive forces (e.g., stress or load).

Figure 8:
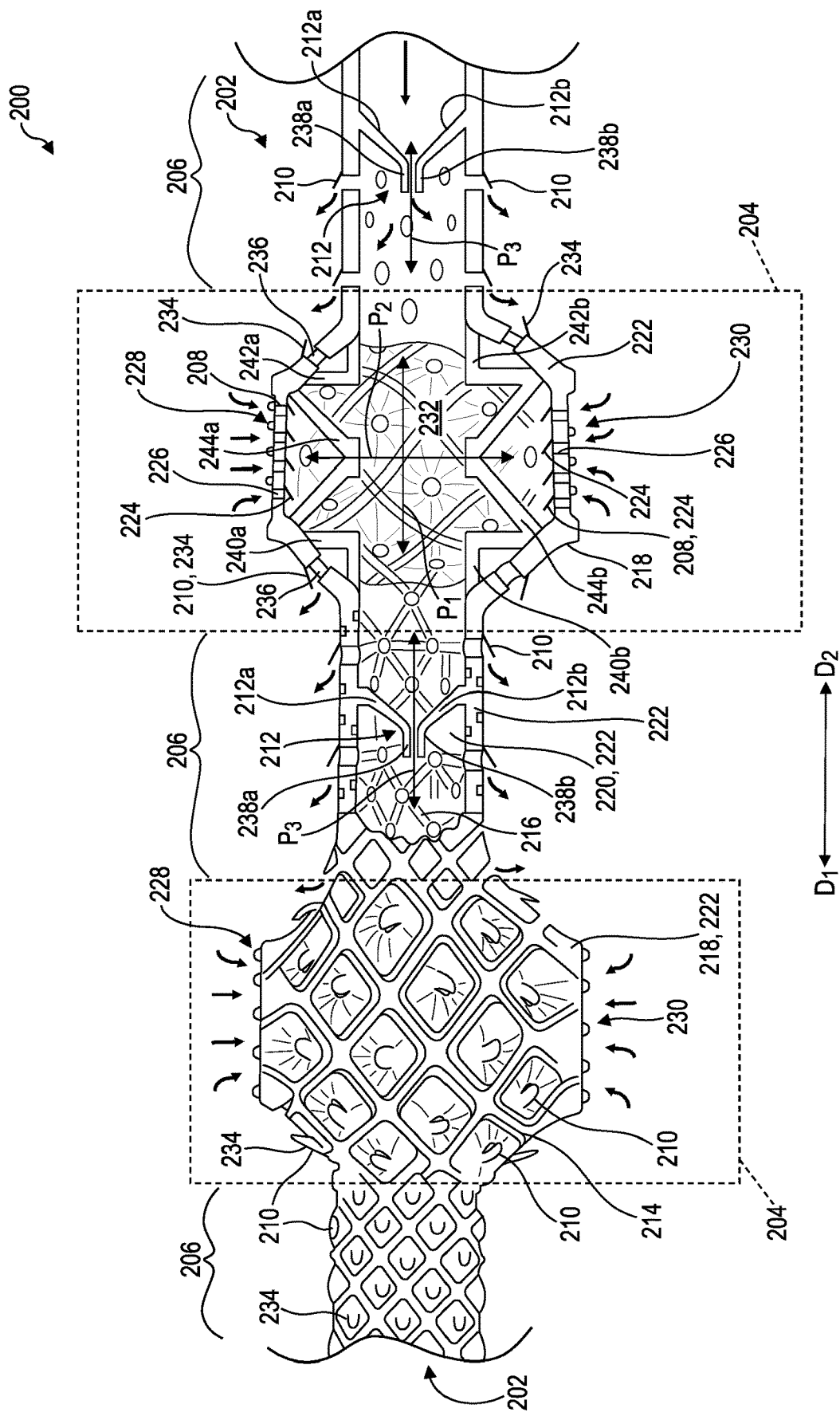
FIG. 8 is a partial cut-away side view of an exemplary adjunct having at least one fluid control feature.

FIG. 8 illustrates one embodiment of an adjunct 200 having a lattice main structure 202 that is formed of unit cells 204. While not shown, the adjunct 200 can be positioned atop an anvil surface of an anvil, like anvil 34 shown in FIG. 1, and/or a top or deck surface of a staple cartridge, like staple cartridge 40 and 102 shown in FIGS. 1 and 6, respectively. In this illustrated embodiment, the unit cells 204 are hollow with passageways, e.g., first passageway denoted by arrow $P_1$ and second passageway denoted by arrow $P_2$, extending therethrough. In use, when a force is applied to the adjunct 200, the unit cells 204 are configured to deform or compress. In this way, the unit cells 204 can function as pumping elements that drive fluid into and out of the adjunct 200. The unit cells 204 are connected to each other via connecting structures 206 that are in the form of hollow tubes with passageways, e.g., passageways denoted by arrow $P_3$, extending therethrough. As a result, the unit cells 204 are in fluid communication with each other such that a continuous network of pathways are present within the adjunct 200. Further, since the connecting structures 206 are in the form of hollow tubes, the connecting structures 206 can also serve as pumping features when the adjunct is being compressed. For purposes of clarity, only unit cells 204 and three connecting structures 206 are being illustrated.

The adjunct 200 can include at least one absorbable sub-structure 208, 210, 212, 214, 216 that is formed in the lattice main structure 202. The at least one absorbable sub-structure 208, 210, 212, 214, 216 can have a variety of configurations. For example, in this illustrated embodiment, the lattice main structure 202 is illustrated as having a variety of different absorbable sub-structures 208, 210, 212, 214, 216 formed therein. More specifically, the absorbable sub-structures 208, 210, 212, 214, 216 include first flapper valves 208, second flapper valves 210, duck bill valves 212, first microchannels 214 that are defined within an exterior surface 218 of a sidewall 222 of the lattice main structure 202, and second microchannels 216 that are defined within interior surface 220 of the sidewall 222 of the lattice main structure 202. The first and second microchannels 214, 216 are each configured to direct fluid therethrough. While a variety of different absorbable sub-structures are illustrated, a person skilled the art will appreciate that the type(s) of absorbable sub-structures and the number of absorbable sub-structures can depend at least upon the size and shape of lattice main structure, and therefore, the adjunct is not limited to the types and number of absorbable sub-structures illustrated in the figures. Further, while a variety of different absorbable sub-structures are illustrated, in other embodiments, the lattice main structure can have any suitable type and number of absorbable sub-structures.

While not illustrated, the adjunct 200 can include at least one drug disposed within the lattice main structure 202. In such instances, a person skilled in the art will appreciate that the fluid can serve as a carrier vehicle for the at least one drug. As such, fluid movement through and out of the adjunct would therefore include drug movement and as a result, it can affect the rate and/or location of drug release from the adjunct.

The first flapper valves 208 can have a variety of configurations. For example, as shown in FIG. 8, the first flapper valves 208 each include a first flap 224, e.g., a movable polymer flap, that is placed over a respective first opening 226 that completely extends through the sidewall 222 of the lattice main structure 202. While the first openings 226 can be positioned at various locations in the sidewall, in this illustrated embodiment, the first openings are positioned at the top portion 228 and the bottom portion 230 of the unit cells 204. In use, the first flap 224 is configured to move from a closed position to an open positon. When the first flap 224 is in an open position, as shown in FIG. 8, fluid (denoted by the arrows) can pass through the respective first opening and into an internal volume 232 of the respective unit cell 204. When the first flap 224 is in a closed position, the first flap 224 creates a seal, and as a result, any fluid within the internal volume 232 of the respective unit cell 204 is inhibited from passing through the respective first opening 226 and out of the adjunct 200. As such, the first flapper valves 208 are configured as one-way self-sealing valves that only allow fluid ingress.

The second flapper valves 210 can have a variety of configurations. For example, as shown in FIG. 8, the second flapper valves 210 each include a second flap 234, e.g., a movable polymer flap, that is placed over a respective second opening 236 that completely extends through the sidewall 222 of the lattice main structure 202. While the second openings 236 can be positioned at various locations in the sidewall 222, in this illustrated embodiment, the second openings 236 are along the sides of the unit cells 204 and around the connecting structures 206. The second flap 234 is configured to move from a closed position to an open position. When the second flap 234 is in an open position, as shown in FIG. 8, fluid (denoted by a black arrow) can pass out of the unit cells 204 and the connecting structures 206, through the respective second openings 236 and out of the adjunct 200. When the second flap 234 is in a closed position, the second flap 234 creates a seal, and as a result, any fluid outside of the adjunct 200 is inhibited from passing through the respective second opening 236 and into the unit cells 204 and the connecting structures 206. As such, the second flapper valves 210 are configured as one-way self-sealing valves that only allow fluid egress.

Figure 9:
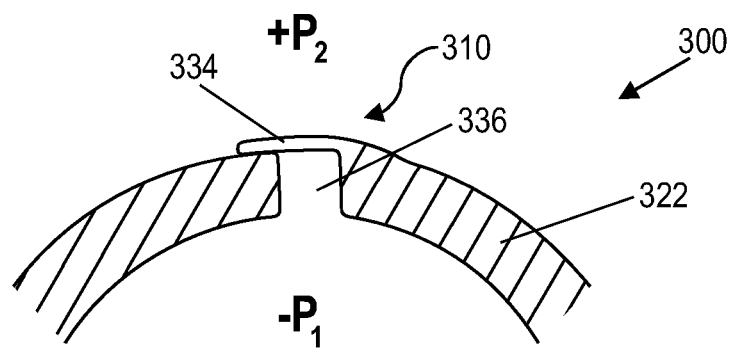
FIG. 9 is a cross-sectional view of a portion of another embodiment of an adjunct having at least one fluid control feature, showing the at least fluid control feature in a closed position.
Figure 10:
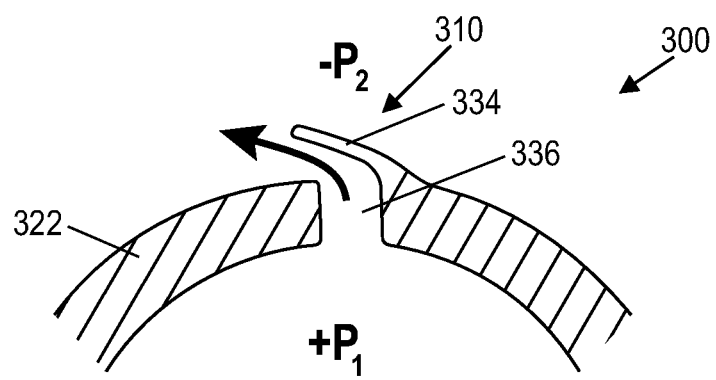
FIG. 10 is a cross-sectional view of the portion of the adjunct of FIG. 9, showing the at least one fluid control feature in an open position.

FIG. 9 and FIG. 10 illustrate another embodiment adjunct 300 with a flapper valve 310, like second flapper valves 210 shown in FIG. 8, that is designed to use a constricting physical bias to allow fluid to move in one direction but prevent movement in the opposite direction. While not shown, the adjunct 300 can be positioned atop an anvil surface of an anvil, like anvil 34 shown in FIG. 1, and/or a top or deck surface of a staple cartridge, like staple cartridge 40 and 102 shown in FIGS. 1 and 6, respectively. For sake of simplicity, a cross-sectional view of a portion of the adjunct 300 is shown in FIG. 9 and FIG. 10. The flapper valve 310 includes a flap 334 that is bias to a closed position (FIG. 9) to seal an opening 336 through a sidewall 322 of the adjunct 300 when the internal pressure $P_1$ (e.g., pressure inside of the adjunct) is less than the external pressure $P_2$ (e.g., pressure outside of the adjunct). However, when the internal pressure $P_1$ is greater than then external pressure $P_2$, the flap 334 is configured to move to an open position (FIG.

10) thereby allowing at least a portion of the contents, e.g., fluid (denoted by a black arrow) within the adjunct 1000 to flow through the opening 336 and out of the adjunct 300. In some embodiments, the pressure differential is created by the fluid present on both sides of the opening 336. As such, when an exterior force is applied to the adjunct 300, the internal pressure $P_1$ can increase to thereby cause the flapper valve 310 to move from a closed position to an open position.

Referring back to FIG. 8, duck bill valves 212 are positioned within the connecting structures 206 that are used to control fluid movement through the connecting structures 206. Each duck bill valve 212 includes a pair of opposing leaflets 212a, 212b that are attached to and extend from the sidewall 222 of the lattice main structure 202 that define the respective connecting structures 206. The leaflets 212a, 212b are configured to move from a closed position, in which the free ends 238a, 238b of the leaflets 212a, 212b are in contact with each other, to an open position, as shown in FIG. 8, in which the free ends 238a, 238b of the leaflets 212a, 212b are spaced apart from one another. When the duck bill valve 212 is in an open position, the space between the free ends 238a, 238b of the leaflets 212a, 212b allow fluid to pass through the respective connecting structure 206 in one direction $D_1$. When the duck bill valve 312 is in a closed position, the contact between the free ends 238a, 238b of the leaflets 212a, 212b, prevent fluid from passing through the respecting connecting structure 206 in the opposite direction D2.

Figure 11:
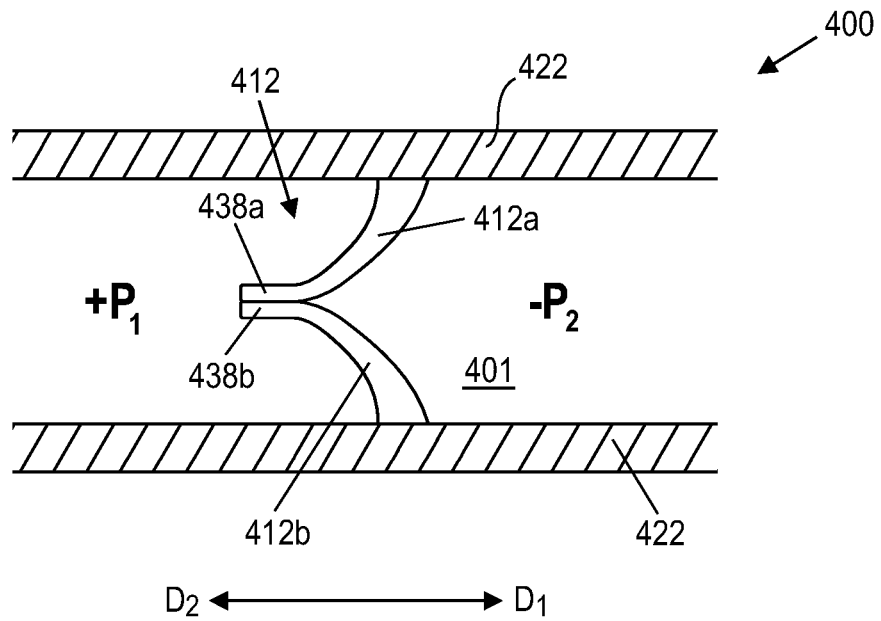
FIG. 11 is a cross-sectional view of a portion of another embodiment of an adjunct having at least one fluid control feature, showing the at least fluid control feature in a closed position.
Figure 12:
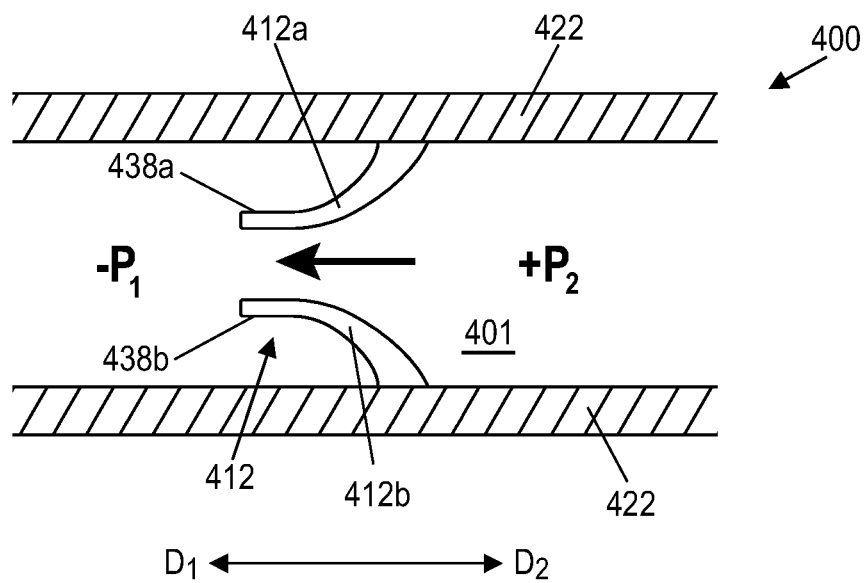
FIG. 12 is a cross-sectional view of the portion of the adjunct of FIG. 11, showing the at least one fluid control feature in an open position.

FIG. 11 and FIG. 12 illustrate another embodiment of an adjunct 400 with a duck bill valve 412, like duck bill valves 212 shown in FIG. 8, that is designed to use a constricting physical bias to allow fluid to move in one direction but prevent movement in the opposite direction. While not shown, the adjunct 400 can be positioned atop an anvil surface of an anvil, like anvil 34 shown in FIG. 1, and/or a top or deck surface of a staple cartridge, like staple cartridge 40 and 102 shown in FIGS. 1 and 6, respectively. For sake of simplicity, a cross-sectional view of a portion of the adjunct 400 with a single duck bill valve 412 is shown in FIG. 11 and FIG. 12. The duck bill valve 412 generally includes two opposing flaps 412a, 412b extending from an annular sidewall 422 of the adjunct 400, in which each flap 412a, 412b has a flattened or bent free end 438a, 438b. As shown in FIG. 11, the flattened or bent free ends 438a, 438b are bias to a closed position (FIG. 11) to seal a passageway 401 through the adjunct 400 when a first pressure $P_1$ on one side of the duck bill valve (e.g., the right side of the duck bill valve) is greater than a second pressure on the opposite side of the duck bill valve (e.g., the left side of the duck bill valve). This prevents fluid from flowing through the valve in a first direction $D_1$. However, when the first pressure $P_1$ is greater than then second pressure $P_2$, the flattened or bent free ends 428a, 438b are configured to move to an open position (FIG. 12) to thereby allow fluid (denoted by a black arrow) to flow through the duck bill valve, and thus through the passageway 401 of the adjunct in a second direction D2. In some embodiments, when an exterior pressure is applied to the adjunct 400, the internal pressure, e.g., the second pressure $P_2$, can increase to thereby cause the duck bill valve to move from a closed position to an open position.

Referring back to FIG. 8, the adjunct 200 can include internal stopping elements 240a, 240b, 242a, 242b, 244a, 244b that are formed in the unit cells 204 and extend into the internal volume 232. These internal stopping elements 240a, 240b, 242a, 242b, 244a, 244b are configured to come into contact with each other to thereby limit the amount of deformation of the respective unit cell 204 while the adjunct 200 is being compressed. While the adjunct 200 can include any number of internal stopping elements, in this illustrated embodiment, the adjunct includes three sets of internal stopping elements 240a, 240b, 242a, 242b, 244a, 244b.

The internal stopping elements 240a, 240b, 242a, 242b, 244a, 244b can have a variety of configurations. Further, the internal stopping elements can have the same or different structural configurations. As shown in FIG. 8, the first set of elements include first and second opposing stopping elements 240a, 240b, each having a L-shaped configuration in which the first stopping element 240a is positioned proximate to the top portion 228 of the unit cell 204 and the second stopping element 240b is positioned proximate to the bottom portion 230 of the unit cell 204. The second set of elements include third and fourth opposing stopping elements 242a, 242b, each having a L-shaped configuration in which the third stopping element 242a is positioned proximate to the top portion 228 of the unit cell 204 and the fourth stopping element 242b is positioned proximate to the bottom portion 230 of the unit cell 204. The first and second sets of elements are positioned on opposite sides of the internal surface of the unit cell 204. The third set of elements include fifth and sixth opposing stopping elements 244a, 244b, each having a V-shaped configuration in which the fifth stopping element 244a is positioned proximate to the top portion 228 of the unit cell 204 and the sixth stopping element 244b is positioned proximate to the bottom portion 230 of the unit cell 204. The third set of elements are positioned between the first and second sets of elements. A person skilled in the art will appreciate that the number and structural configurations of the internal stopping elements depend at least upon the structural configuration and size of the unit cell, and therefore, in other embodiments, a unit cell can have a different number of internal stopping elements and/or internal stopping elements having other suitable shapes and sizes.

Figure 13:
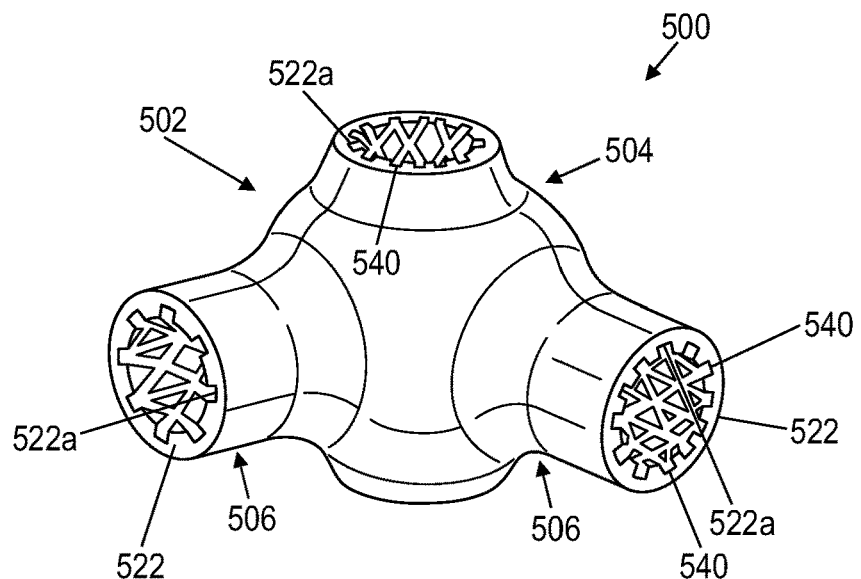
FIG. 13 is a perspective side view of a portion of another exemplary embodiment of an adjunct having at least one fluid control feature.
Figure 14:
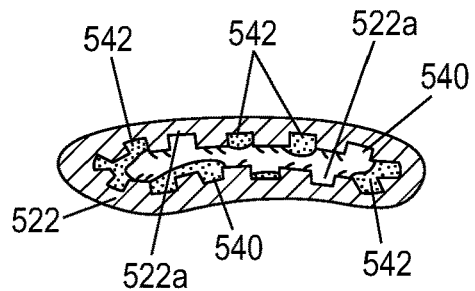
FIG. 14 is a cross-sectional front view of one of a connecting structure of the adjunct of FIG. 13 with fluid within at least one fluid control feature, showing the adjunct in a compressed state.

FIG. 13 illustrates another embodiment of an adjunct 500 having a lattice main structure 502 that is formed of interconnected unit cells 504. While not shown, the adjunct 500 can be positioned atop an anvil surface of an anvil, like anvil 34 shown in FIG. 1, and/or a top or deck surface of a staple cartridge, like staple cartridge 40 and 102 shown in FIGS. 1 and 6, respectively. For sake of simplicity, only one unit cell 504 and a portion of two connecting structures 506 are being illustrated. While the unit cell 504 and the two connecting structures 506 can have a variety of configurations, in this illustrated embodiment, the unit cell 504 is a hollow structure and the two connecting structures 506 are each a hollow tube. As shown in FIG. 5, the unit cell 504 and the hollow tubes 506 each have microchannels 540 formed therein, i.e., smaller channels located within the macrochannels defined by the hollow tubes. That is, the microchannels 540 are formed within the sidewall 522 of the lattice main structure 502 that define the unit cell 504 and the two hollow tubes 506. In this illustrated embodiment, the microchannels 540 form part of the internal surface 522a of the sidewall 522. In use, when the adjunct 500 is compressed, the fluid 542 within the adjunct 500 can be directed via the microchannels 540, for example, as shown in FIG. 14.

Figure 15:
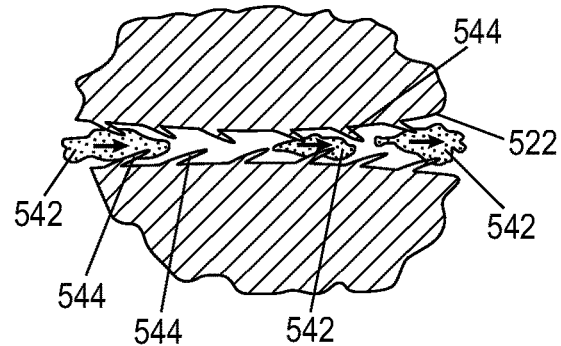
FIG. 15 is a magnified cross-sectional side view of one of the at least fluid control feature of FIG. 14 having an additional fluid control features formed therein, showing fluid movement through the at least one fluid control feature.

In certain embodiments, the microchannels 540 can include microfeature(s) that are oriented within the microchannels 540 so as to direct fluid 542 therethrough in a predefined direction. For example, as illustrated in FIG. 15, a microchannel 540 can include flexible wicking elements 544 that are configured to direct fluid 542 though the microchannel 540 in a first direction $D_1$. A person skilled in the art will appreciate that the orientation of the microfeature(s) depend at least upon the structural configuration of the microchannel and the desired direction of fluid flow therethrough.

In some embodiments, the microchannels can be configured to wick fluid therethrough via capillary action. For example, the microchannels can have a width of about 10 micrometers to 500 micrometers so as to wick fluids therethrough via capillary action. In other embodiments, the microchannels can include knitted or woven construction of filaments that are configured to wick fluids therethrough.

Figure 16:
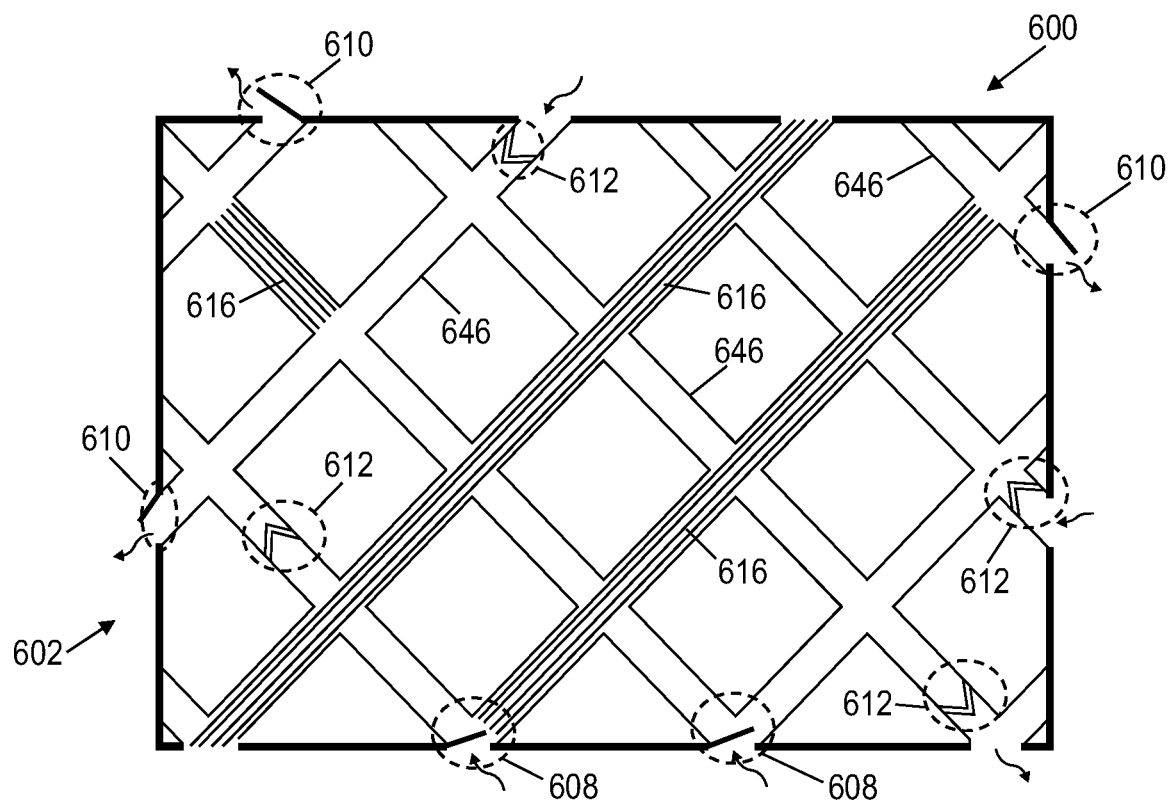
FIG. 16 is a cross-sectional side view of another exemplary embodiment of an adjunct having at least one control feature.

FIG. 16 illustrates another exemplary embodiment of an adjunct 600 having a lattice main structure 602 with absorbable sub-structures 608, 610, 612, 616 that are formed in the lattice main structure 602. While not shown, the adjunct 600 can be positioned atop an anvil surface of an anvil, like anvil 34 shown in FIG. 1, and/or a top or deck surface of a staple cartridge, like staple cartridge 40 and 102 shown in FIGS. 1 and 6, respectively. The lattice main structure includes hollow struts 1646 in which the absorbable sub-structures are formed for controlling fluid flow therethrough. While the absorbable sub-structures 608, 610, 612, 616 can have a variety of configurations, in this illustrated embodiment, the absorbable sub-structures 608, 610, 612, 616 include first flapper valves 608, second flapper valves 610, duck bill valves 612, and microchannels 616. Fluid flow into and out of the adjunct is denoted by the arrows. The first flapper valves 608, the second flapper valves 610, the duck bill valves 612, and the microchannels 616 are similar in structural configuration and/or function to the first flapper valves 208, the second flapper valves 210, the duck bill valves 212, and the second microchannels 216 shown in FIG. 8 and therefore are not described in detail herein.

Figure 17:
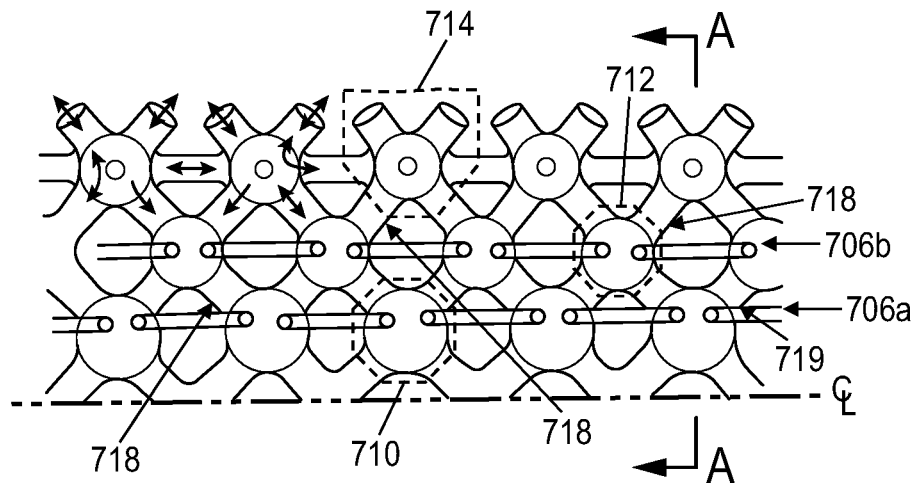
FIG. 17 is a top-down view of an exemplary embodiment of a stapling assembly having an adjunct releasably retained on a staple cartridge, showing only a portion of the stapling assembly.
Figure 18:
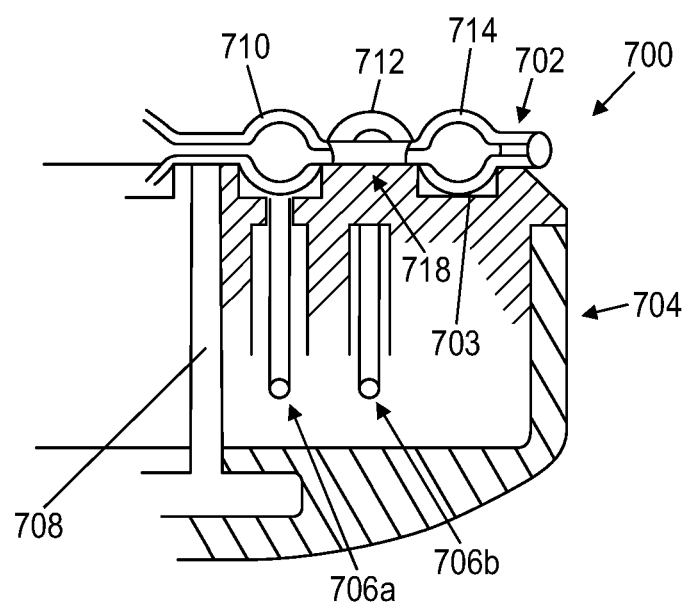
FIG. 18 is a cross-sectional view of the stapling assembly of FIG. 17 taken at A-A.

In some embodiments, at least a portion of the unit cells of an adjunct can be positioned within regions of the adjunct that do not overlap with staple rows of a cartridge when the adjunct is released retained thereto, for example as shown in FIG. 17 and FIG. 18. As such, in use, the non-overlapping unit cells can serve as pumping elements that are configured to drive fluid out of the adjunct when the unit cells are being compressed, draw fluid into the adjunct when the unit cells are expanding back to their uncompressed configuration, or a combination thereof.

FIG. 17 and FIG. 18 illustrate an exemplary embodiment of a stapling assembly 700 having an adjunct 702 releasably retained on a top or deck surface 703 of a staple cartridge 704 (e.g., the cartridge surface that faces the anvil). As shown, only one half (e.g., the right half) of the adjunct 702 is illustrated on the staple cartridge 704 with two rows of staples 706a, 706b disposed within the staple cartridge 704. As shown in FIG. 18, the inner most staple row 706a is adjacent a knife slot 708 defined within the cartridge 704.

While the adjunct 702 can have a variety of configurations, the adjunct 702 is formed of interconnected unit cells (e.g., Schwarz-P structures) that are arranged in two sets of three longitudinal arrays, with the first set positioned on a first side of the intended cut line $C_L$ of the adjunct 702 and the second set (not shown) positioned on the second side of the intended cut line $C_L$ of the adjunct 702. Since both sets are the same, only unit cells 710, 712, 714 of one set of the three longitudinal arrays are illustrated in FIG. 17 and FIG. 18. Further, adjacent unit cells are connected to each other via connecting structures 718.

As shown in FIG. 17 and FIG. 18, the inner-most longitudinal array of unit cells 710 overlap with the first staple row 706a (e.g., the inner-most staple row) and the intermediate longitudinal array of unit cells 712 overlap with the second staple row 706b (e.g., the outer-most staple row). Further, the outer-most longitudinal array of unit cells 714 do not overlap with any of the staple rows 706a, 706b. Further, the outer-most longitudinal array of unit cells 714 do not overlap with intended cut line $C_L$ of the adjunct or the knife slot 708 of the cartridge 704. As a result, in use, when the adjunct 702 is stapled and cut, the staples 706a, 706b and cutting element (not shown) do not puncture and cut, respectively, the outer-most longitudinal array of unit cells 714. This allows the structural integrity of the outer-most longitudinal array of unit cells 714 to remain intact. As such, at least the outer-most longitudinal array of unit cells 714 can draw fluid into the adjunct when being compressed, drive fluid out of the adjunct when expanding to uncompressed configuration, or a combination thereof, as denoted by the arrows in FIG. 17.

Figure 19:
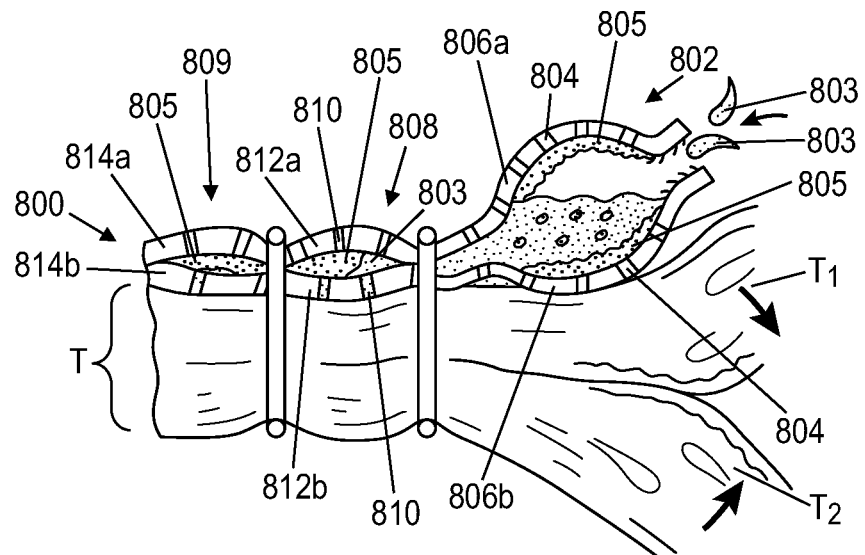
FIG. 19 is a partial-schematic illustrating an exemplary embodiment of an adjunct in a tissue deployed state, showing the tissue in a first position.
Figure 20:
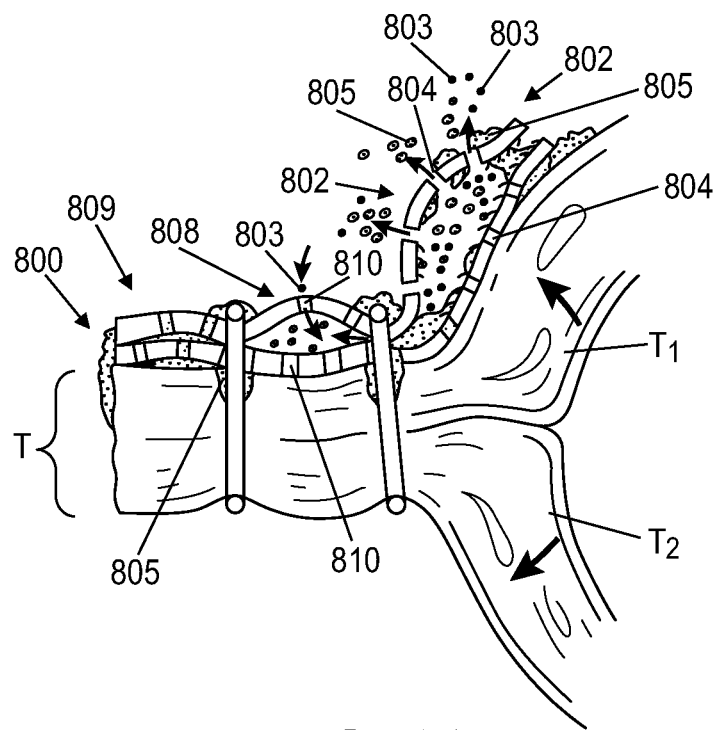
FIG. 20 is a partial-schematic illustrating the adjunct of FIG. 19, showing the tissue in a second position.

In certain embodiments, as tissue moves, the non-overlapping unit cells of the adjunct relative to the staple rows and knife slot of the cartridge can be configured to draw fluid into the adjunct or pump out fluid and/or fluid/drug mixture to surrounding tissue. For example, in FIG. 19, an adjunct 800 is stapled to tissue T. As shown, the non-overlapping unit cells 802 (e.g., the outer-most longitudinal array of unit cells), only one of which is illustrated, can draw fluid 803 into the adjunct 800 when segments of the tissue $T_1$ and $T_2$ move towards each other. The drawn fluid can be used to saturate the at least one drug 805 (e.g., powered drug) that is positioned along the inner surface 802a of the unit cell 802. When segments of the tissue $T_1$ and $T_2$ move away from each other, as shown in FIG. 20, the non-overlapping unit cell 802 can be configured to pump fluid 803 and the at least one drug 805 out of the adjunct 800, e.g., through microholes 804 extending through the top and bottom walls 806a, 806b of the unit cell 802. Further, other unit cells, e.g., adjacent unit cell 808, 809, can be configured to draw fluid into and out of the adjunct, e.g., through microholes 810 extending through respective top and bottom walls 812a, 812b, 814a, 814b. As such, the drawn fluid can be used to saturate the at least one drug 805 positioned with the respective unit cells 808, 809 of the unit cell 802, and thus, as shown in FIG. 20, the respective unit cells 808, 809 can be configured to pump the fluid 803 and the at least one drug 805 therefrom.

As noted above, the present adjuncts can contain at least one drug. The at least one drug can be positioned at various locations within the adjunct (e.g., within one or more reservoirs that are formed within the adjunct). For example, in embodiments wherein the adjunct includes hollow unit cells, the at least one drug can be contained within the internal volume of the unit cell. Alternatively, or in addition, the at least one drug can be contained within a void or pocket defined within a wall of the unit cell. In some embodiments, a first drug of the at least one drug can be positioned within the adjunct such that it is free to be expelled in response to fluid ingress into and through the adjunct, and a second drug of the at least one drug can be positioned within the adjunct such that it is expelled in response to structural degradation of at least a portion of the adjunct. As a result, in certain embodiments, drug delivery can be dependent not only on fluid movement, but in some instances, time (hydrolysis) and/or oxygen level (e.g., enzyme degradation).

Figure 21:
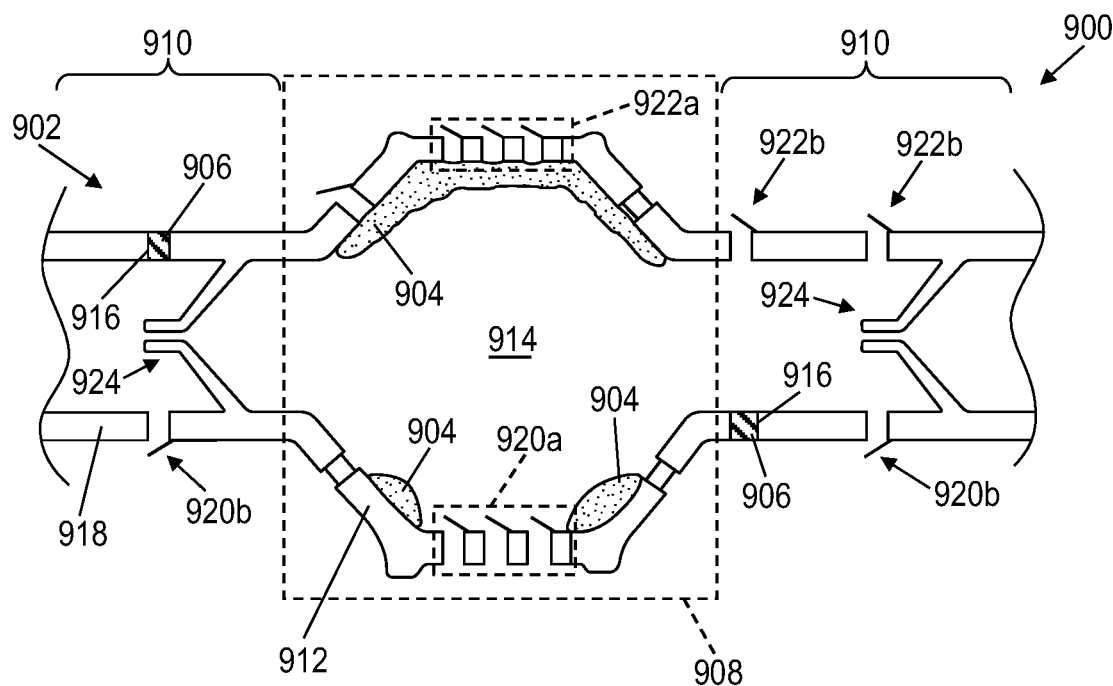
FIG. 21 is a cross-sectional view of a portion of another exemplary embodiment of an adjunct having at least one drug disposed therein and at least one fluid control feature.

FIG. 21 illustrates an exemplary embodiment of an adjunct 900 having a hollow lattice macrostructure 902 with at least one drug 904, 906 contained therein. While not shown, the adjunct 900 can be positioned atop an anvil surface of an anvil, like anvil 34 shown in FIG. 1, and/or a top or deck surface of a staple cartridge, like staple cartridge 40 and 102 shown in FIGS. 1 and 6, respectively. The hollow lattice macrostructure 902 is formed of unit cells 908 that are connected to each other via connecting structures 910. While the unit cells 908 and connecting structures 910 can have a variety of configurations, in this illustrated embodiment, the unit cells 908 have an outer wall 912 that defines an internal cavity 914, and the connecting structures 910 are in the form of hollow tubes. For purposes of simplicity, only one unit cell 908 and two connecting structures 910 are illustrated. As shown, a first drug 904 is disposed within the internal cavity 914 (e.g., a primary reservoir) of the unit cell 908, and a second drug 906 is disposed within voids 916 (e.g., a secondary reservoir) defined within the wall 918 of the connecting structures 910. In certain embodiments, the internal cavity 914 is configured to release at least a portion of the first drug 904 therefrom in response to an initial ingress of fluid into the unit cell 908, whereas the voids 916 can be configured to release at least a portion of the second drug 906 therefrom in response to structural degradation of the portions of the wall 918 that define the voids 916.

As further shown, absorbable sub-structures 920a, 920b, 922a, 922b, 924 are formed in hollow lattice macrostructure 902. More specifically, absorbable sub-structures 920a, 922a are formed in the unit cell 908 and absorbable sub-structures 920b, 922b, 924 are formed in the connecting structures 910. While the absorbable sub-structures 920a, 920b, 922a, 922b, 924 can have a variety of configurations, in this illustrated embodiment, the absorbable sub-structures 920a, 920b, 922a, 922b, 924 include first flapper valves 920a, 920b, second flapper valves 922a, 922b, and duck bill valves 924. The first flapper valves 920a, 920b, the second flapper valves 922a, 922b, and the duck bill valves 924 are similar in structural configuration and/or function to the first flapper valves 208, the second flapper valves 210, and the duck bill valves 212 shown in FIG. 8 and therefore are not described in detail herein.

In use, when a force is applied to the adjunct 900, the unit cells 908 are configured to deform or compress. In this way, the unit cells 908 can function as pumping elements that draw fluid into and out of the adjunct 900. The influx of fluid can be directed through the adjunct 900 to thereby mix with at least the first drug 904 and/or the second drug 906. The resulting fluid/drug mixture can then be subsequently driven out of the adjunct 200 via, e.g., the pumping action of the unit cells 908. As such, the unit cells 908 can direct drug movement through the adjunct 900 and control the location of drug elution from the adjunct 900. Further, the flow of the fluid and/or the fluid/drug mixture can be further controlled by the absorbable sub-structures 920a, 920b, 922a, 922b, 924. That is, the absorbable sub-structures 920a, 920b, 922a, 922b, 924 can also be used to control the rate and/or direction of drug movement through and out of the adjunct 900. As such, the combination of the unit cells with the absorbable sub-structures can effect controlled drug delivery of the first and second drugs from the adjunct.

Figure 22:
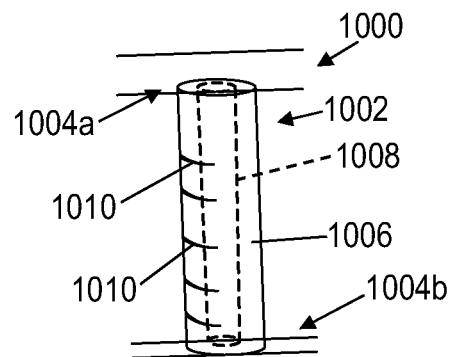
FIG. 22 is a cross-sectional view of a portion of another exemplary embodiment of an adjunct, showing the adjunct in an uncompressed state.
Figure 23:
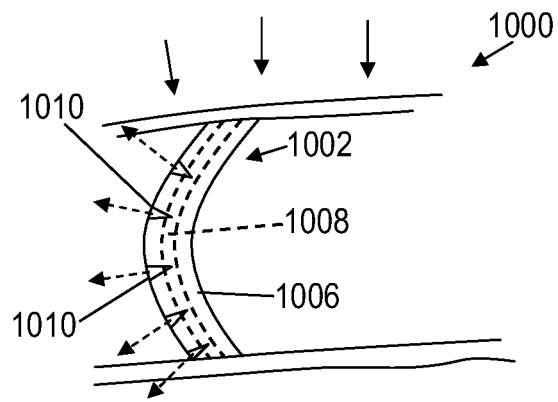
FIG. 23 is a cross-sectional view of the adjunct of FIG. 22, showing the adjunct in a compressed state.

Other structural configurations and mechanisms can be used for adjunct drug delivery. For example, as shown in FIG. 22 and FIG. 23, an adjunct 1000 can include buckling columns 1002, only one of which is illustrated, that extend from a first end 1004a to a second end 1004b with a longitudinal axis LA extending therebetween. While not shown, the adjunct 1000 can be positioned atop an anvil surface of an anvil, like anvil 34 shown in FIG. 1, and/or a top or deck surface of a staple cartridge, like staple cartridge 40 and 102 shown in FIGS. 1 and 6, respectively. While the buckling columns 1002 can have a variety of configurations, in this illustrated embodiment, the buckling column 1002 has an elongated cylindrical body 1006 with a longitudinal channel 1008 that extends from the first end 1004a to the second end 1004b of the body 1006. The longitudinal channel 1008 is configured to draw fluid therein and thus into the adjunct 1000 (e.g., when the adjunct 1000 is stapled to tissue). The buckling column 1002 also includes lateral slots 1010 that are defined within the body 1006 and are in fluid communication with the longitudinal channel 1008. The lateral slots 1010 are configured to house at least one drug (not shown). As shown in FIG. 22, when the adjunct 1000 is uncompressed (e.g., without having a force applied to it), the buckling column 1002 is in a generally straight configuration. As a result, the lateral slots 1010 are closed, and therefore drug contained therein would be sealed within the respective lateral slot 1010.

Once a force (depicted as solid arrows) is applied to the adjunct 1000, as shown in FIG. 22, the adjunct compresses causing the buckling column to bend (e.g., into a convex configuration) and the lateral slots 1010 to open. This causes the at least one drug contained within the lateral slots 1010, now open, and fluid present within the longitudinal channel 1008 to be expelled (depicted as dotted arrows) from the adjunct 1000. That is, once the lateral slots 1010 are open, the expulsion of the fluid present within the longitudinal channel 1008 through the lateral slots 1010 causes the at least one drug to be released from the buckling columns 1002, and thus out of the adjunct 1000. While only five lateral slots are illustrated in FIG. 22 and FIG. 23, a person skilled in the art will appreciate that the number of lateral slots can vary and can depend at least upon the structural configuration of the buckling column, and therefore the number of lateral slots are not limited to what is illustrated in the figures. It is also contemplated herein that in other embodiments, the at least one drug can be omitted from at least one or more lateral slots within the buckling columns and/or the adjunct can also additional buckling columns with lateral slots that do not contain any drug therein.

Figure 24:
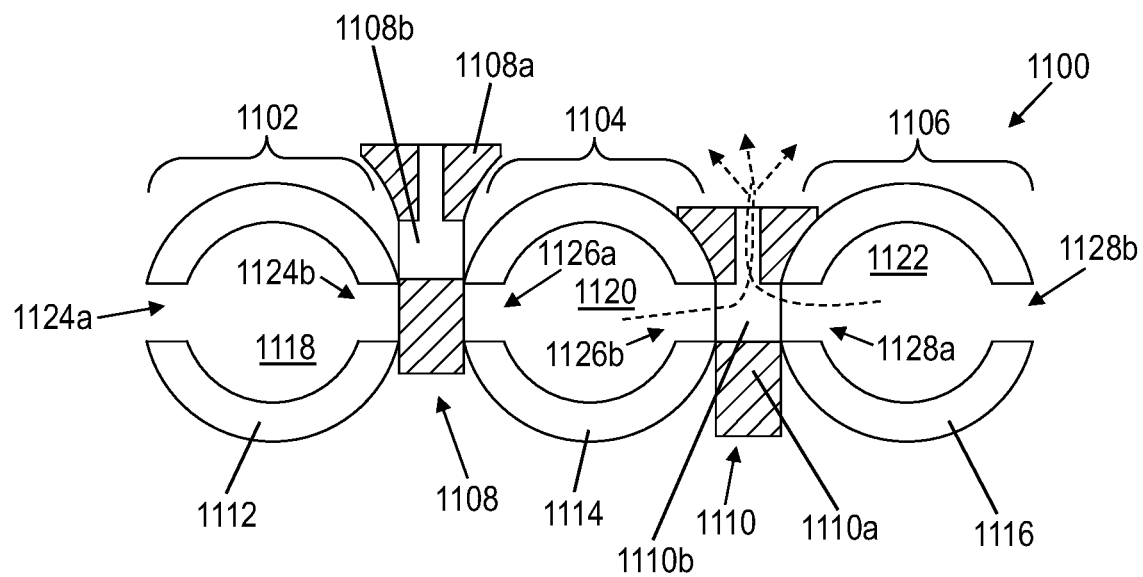
FIG. 24 is a cross-sectional view of another exemplary embodiment of an adjunct having a least one control feature.

In other embodiments, the adjunct can include sliding valves that open under pressure (e.g., pressure exerted during stapling or by the tissue stapled to the adjunct). For example, as shown in FIG. 24, an adjunct 1100 is formed of unit cells 1102, 1104, 1106 with drug (not shown) disposed therein and sliding valves 1108, 1110. While not shown, the adjunct 1100 can be positioned atop an anvil surface of an anvil, like anvil 34 shown in FIG. 1, and/or a top or deck surface of a staple cartridge, like staple cartridge 40 and 102 shown in FIGS. 1 and 6, respectively. For simplicity, only three unit cells 1102, 1104, 1106 and two sliding valves 1108, 1110 are illustrated. More specifically, sliding valve 1108, which is shown in a closed position, is located between adjacent unit cells 1102 and 1104, and sliding valve 1110, which is shown in an open position, is located between adjacent unit cells 1104 and 1106.

While the unit cells 1102, 1104, 1106 can have variety of configurations, each unit cell is defined by a respective wall 1112, 1114, 1116 having a circular-shaped configuration with an internal cavity 1118, 1120, 1122 defined therein. Each wall 1112, 1114, 1116 also includes two opposing channels 1124a, 1124b, 1126a, 1126b, 1128a, 1128b. Further, while the sliding valves 1108, 1110 can have a variety of configuration, as shown in FIG. 24, each sliding valve 1108, 1110 has a body 1108a, 1110a with a T-shaped channel 1108b, 1110b defined therein that is configured to allow fluid flow through the sliding valve 1108, 1110. In use, the sliding valves 1108, 1110 move up and down relative to the unit cells 1102, 1104, 1106 when a force is being applied to the adjunct 1100 (e.g., during stapling or by tissue when the adjunct is stapled thereto). As such, when the sliding valves 1108, 1110 are in a closed position, such as illustrated sliding valve 1108, the T-shaped channel 1108b is not aligned, and therefore not in fluid communication with the channels 1124b, 1126a of the adjacent unit cells 1102, 1104. As a result, this prevents the fluid or fluid/drug mixture that is present within the unit cells 1102, 1104 from being released from the adjunct 1100. However, when the sliding valves 1108, 110 are in an open position, such illustrated sliding valve 1110, the T-shaped channel 1110b is aligned with, and therefore in fluid communication with the channels 1126b, 1128a of the adjacent unit cells 1104, 1106. As a result, the fluid or fluid/drug mixture that is present within the adjacent unit cells 1104, 1106 can be released (depicted as dotted arrows) from the adjunct 1100.

Figure 25:
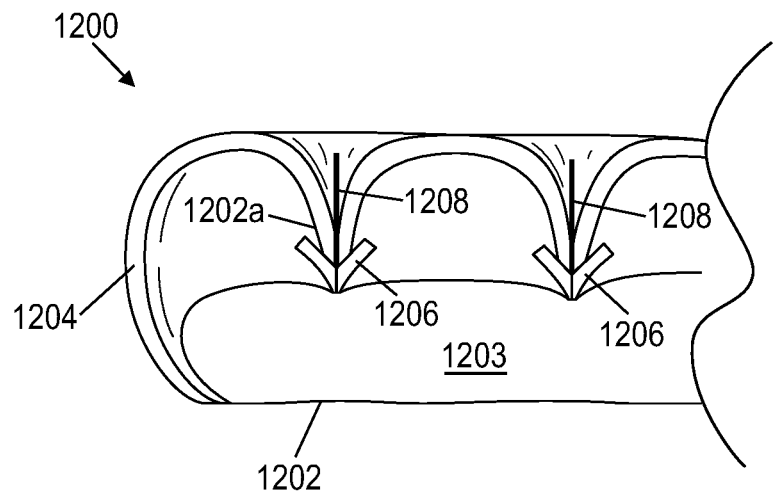
FIG. 25 is a side view of an exemplary embodiment of an adjunct drug delivery system, showing the system in an uncompressed state.
Figure 26:
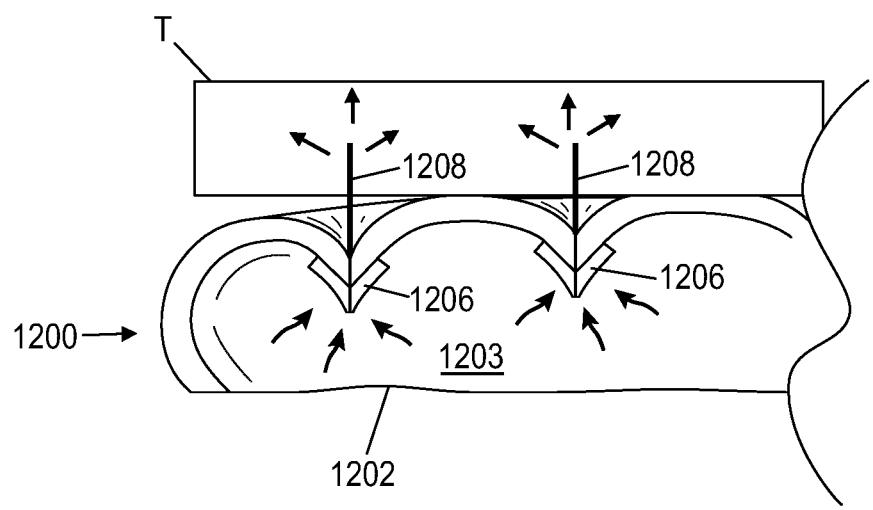
FIG. 26 is a side view of the adjunct drug delivery system of FIG. 25, showing the system in a compressed state.

In some embodiments, adjunct drug delivery systems can be configured to administer drugs directly into the tissue, as opposed to just onto the tissue surface. For example, as shown in FIG. 25 and FIG. 26, an adjunct drug delivery system 1200 can include a compressible drug pouch 1202 having an internal cavity 1203 that houses at least one drug (not shown) therein. The system 1200 also includes a needle carrier 1204 that is coupled to the drug pouch 1202. The needle carrier 1204 includes piercing members 1206 with at least one drug delivery needle 1208 attached thereto. As shown, the needle carrier curves about the drug pouch 1202 such that the piercing members face the top surface 1202a of the drug pouch 1202. When the adjunct drug delivery system 1200 is compressed (e.g., when stapled to tissue), for example, as shown in FIG. 26, the piercing members 1206 pierce through the top surface 1202a and into the internal cavity 1203 of the drug pouch 1202. As a result, the internal cavity 1203 of the drug pouch 1202 and the drug delivery needles 1208 are then in fluid communication with each other to thereby allow the at least one drug to be expelled from the drug pouch 1202. Further, when the adjunct system 1200 is placed and compressed against tissue T, as shown in FIG. 26, the drug delivery needles 1208 pierce into the tissue and therefore deliver the at least one drug directly into the tissue T (depicted as solid arrows). While not shown, the adjunct drug delivery system 1200 can be positioned atop an anvil surface of an anvil, like anvil 34 shown in FIG. 1, and/or a top or deck surface of a staple cartridge, like staple cartridge 40 and 102 shown in FIGS. 1 and 6, respectively.

In other embodiments, adjuncts can be configured to apply medicants to staples as the staples are deployed therethrough. For example, the unit cells 710 shown in FIG. 17 and FIG. 18 that overlap staple rows 706a, 706b can be configured to house drug therein. In this way, as the staples deploy through respective unit cells 710, the drug can be applied to the staples.

Figure 29:
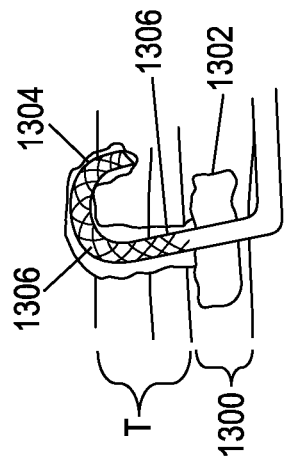
FIG. 29 is a cross-sectional view of the adjunct of FIG. 28, showing the staple leg in a completely deployed state.
Figure 28:
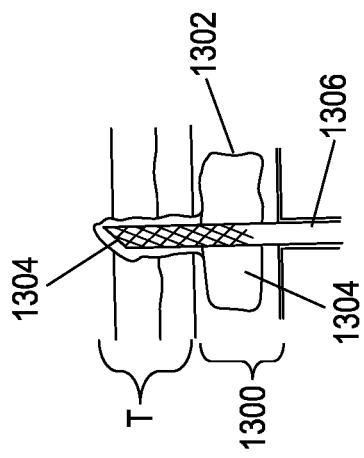
FIG. 28 is a cross-sectional view of the adjunct of FIG. 27 showing the adjunct placed against tissue and the staple leg in a partially deployed state.
Figure 27:
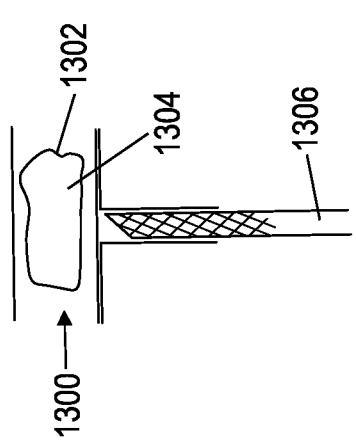
FIG. 27 is a cross-sectional side view of a portion of another exemplary embodiment of an adjunct having at least one drug pocket, showing the portion of the adjunct placed over a staple leg.

In another example, as illustrated in FIG. 27, FIG. 28, and FIG. 29, an adjunct 1300 can include drug pockets 1302 defined therein and that are configured to house drug 1304. As shown, the drug pockets 1302 are positioned within regions of the adjunct 1300 that overlap with staple legs 1306 (e.g., staple legs disposed within a staple cartridge). For simplicity only, one drug pocket 1302 and one staple leg 1306 is illustrated. As a result, when the staple leg 1306 is deployed, the staple leg 1306 penetrates through the drug pocket 1302 (FIG. 28 and FIG. 29) such that the drug 1304 coats onto the staple leg 1306. This allows penetration of drug directly into the tissue T via the coated staple leg 1306 (see FIG. 28 and FIG. 29). Further, in certain embodiments, at least a portion of the staple legs can be textured (illustrated as hatch marking in FIG. 27, FIG. 28, and FIG. 29) to enhance the coating of the drug to the staple legs as they pass though the drug pockets. For example, the textured surface can make the staples hydrophilic or allow the drug to otherwise stick to the staples.

Asymmetric Drug Delivery

As noted above, in certain embodiments, the adjunct can have at least one drug disposed therein. While the adjunct can be configured to release the at least one drug in a variety of ways, in certain embodiments, the adjunct be configured to have an asymmetric drug delivery profile relative to the geometry of the adjunct. For example, the adjunct can have an intended cut line that extends along a longitudinal axis extending from a first end to a second end of the adjunct material, a retaining segment on a first side of the intended cut line and a removing segment on a second side of the intended cut line. In such instances, the adjunct material can have a geometry that is configured to locally deliver or store the at least one drug relative to the intended cut line or relative to the retaining and removing segments. As a result, the adjunct has an asymmetric drug delivery profile of the at least one drug in at least one predetermined direction when the adjunct material is in a tissue deployed state. Stated differently, the at least one drug can be non-uniformly dispersed throughout the adjunct and/or non-uniformly directed through the adjunct such that the drug release profile of the at least one drug from the adjunct in at least one predetermined direction differs along the adjunct.

Figure 30:
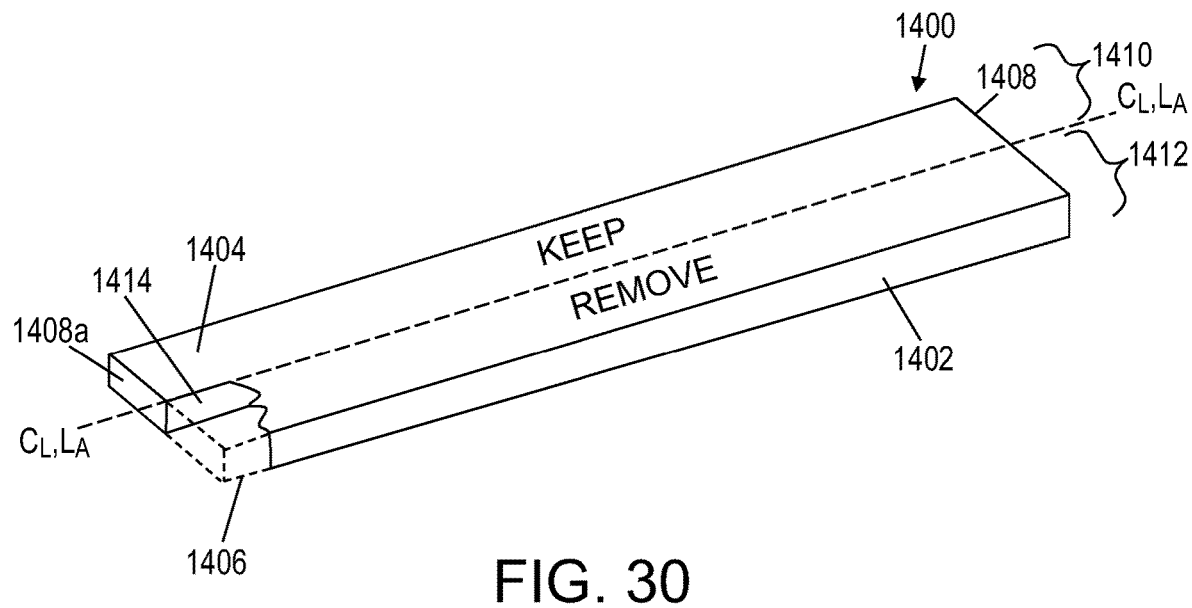
FIG. 30 is perspective view of another exemplary embodiment of an adjunct.

FIG. 30 illustrates an exemplary embodiment of an adjunct 1400 having a lattice structure 1402 with a tissue-contacting surface 1404 and a cartridge-contacting surface 1406 that is opposite the tissue-contacting surface 1404. While not shown, the adjunct 1400 can be positioned atop an anvil surface of an anvil, like anvil 34 shown in FIG. 1, and/or a top or deck surface of a staple cartridge, like staple cartridge 40 and 102 shown in FIGS. 1 and 6, respectively. Since the lattice structure 1402 can be formed by any of the unit cells disclosed herein, the lattice structure 1402 is generally illustrated without any specific unit cells. A person skilled in the art will appreciate that the lattice structure can be formed of strut-based unit cells (e.g., defined by planar hollow struts), strut-less based unit cells (e.g., defined by Schwarz-P structures), or a combination thereof.

As shown, the adjunct 1400 has an intended cut line $C_L$ that extends along a longitudinal axis $L_A$ that extends from a first end 1408a to a second end 1408b of the adjunct 1400. In this illustrated embodiment, the intended cut line $C_L$ divides the adjunct 1400 into a retaining segment 1410 that is configured to remain with the patient (e.g., once the adjunct 1400 is stapled to tissue and cut) and a removing segment 1412 that is configured to be removed from the patient (e.g., once the adjunct 1400 is stapled to tissue and cut). Thus, the retaining segment 1410 remains at the surgical site.

The adjunct 1400 can include at least one drug (not shown) disposed therein. In such embodiments, the at least on drug can be stronger on one side of the adjunct 1400, only present on one side of the adjunct 1400, or have differing effects from one side to the adjacent side of the adjunct 1400. This can result in an asymmetric drug release profile of the at least one drug in at least one predetermined direction from the adjunct 1400. For example, in some embodiments, only the retaining segment 1410 of the adjunct 1400 has at least one drug disposed therein. In this way, the removing segment 1412 does not include the at least one drug, thereby reducing manufacturing costs of the adjunct. The lack of drug within the removing segment 1412 can also prevent the tissue specimen stapled to the removing segment 1412 from being compromised by the at least one drug, and therefore, the tissue specimen would be "cleaner" for biopsy purposes. In other embodiments, the retaining segment 1410 and the removing segment 1412 can be different in at least one of concentration and type of the at least one drug. In certain embodiments, the tissue-contacting surface 1404 of the retaining segment 1410 can have a first drug (e.g., a therapeutic agent) disposed thereon and a portion 1414 of the retaining segment 1410 along the intended cut line CL can have a second drug disposed thereon (e.g., a hemostatic agent).

In other embodiments, the tissue-contacting surface 1404 and cartridge-contacting surface 1406 can differ from each other in at least of concentration and type of the at least one drug. This can result in asymmetric doses of the at least one drug relative to the geometry of the adjunct 1400. For example, in certain embodiments, the tissue-contacting surface 1404 can have a first drug disposed thereon and the cartridge-contacting surface 1406 can have a second drug disposed thereon that is different than the first drug. For example, the first drug can be healing promoting agent(s) and the second drug can be anti-adhesion medicant(s). In some embodiments, the tissue-contacting surface 1404 can be designed with larger pores and more compliance compared to that of the cartridge-contacting surface 1406, which can be designed to prevent staple leg pull through or tearing.

Figure 31:
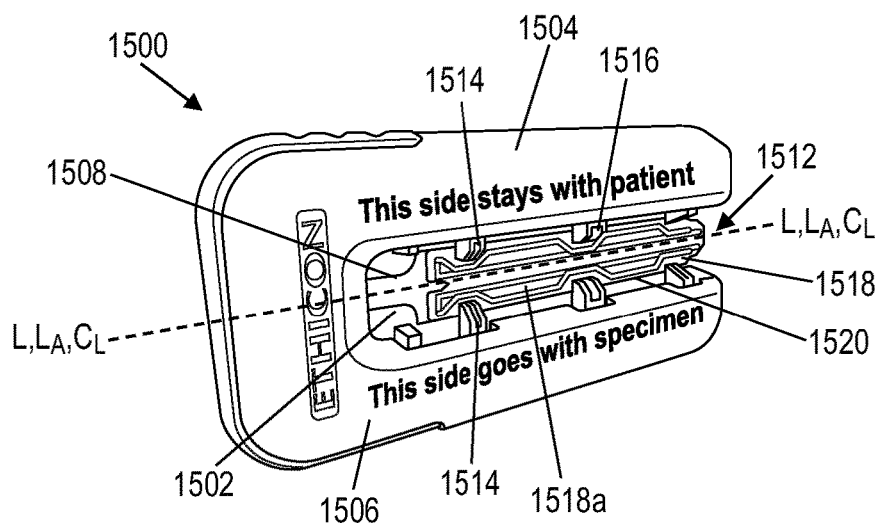
FIG. 31 is a perspective view of an exemplary embodiment of an adjunct applicator having an exemplary embodiment of an adjunct releasably retained thereon.

In some embodiments, the adjunct 1400 can include an indicator feature that is configured to indicate at least one of the retaining segment 1410 of the adjunct 1400 and the location of the at least one drug within the adjunct 1400. The indicator feature can be a visual indication, such an indicia (FIG. 30) or a color (FIG. 31). For example, as shown in FIG. 30, the retaining segment 1410 of the adjunct 1400 includes, and therefore is indicated by, the word "KEEP" printed thereon, and the removing segment 1412 of the adjunct 1400 includes, and therefore is indicated by, the word "REMOVE" printed thereon. Alternatively, or in addition, the indicator feature can configured to indicate the side of the adjunct that is applied to a staple cartridge (e.g., a cartridge-contacting surface), the side of the adjunct that is applied to a tissue (e.g., a tissue-contacting surface), or a combination thereof. As such, the adjunct can include indicator features that are configured to identify the proper orientation of the adjunct relative to a staple cartridge, the patient, or a combination thereof.

In some embodiments, adjuncts can be applied to a staple cartridge and/or an anvil using an adjunct applicator as shown, for example, in FIG. 31. FIG. 31 illustrates an embodiment of an adjunct applicator 1500 having a U-shaped configuration with a channel 1502 extending therethrough. The channel 1502 extends longitudinally along the longitudinal axis L of the adjunct applicator 1500 and divides the adjunct applicator 1500 into a first longitudinal segment 1504 and a second longitudinal segment 1506. An elongated base member 1508 is positioned within and extends along the channel 1502. The adjunct applicator 1500 has a cartridge-facing side 1515 and an anvil-facing side (obstructed) that is opposite the cartridge-facing side. For sake of simplicity, only the cartridge-facing side 1515 of the adjunct applicator 1500 is illustrated. The anvil-facing side of the adjunct applicator is similar to the cartridge-facing side, and therefore a person skilled in the art will appreciate that the following description is also applicable to the anvil-facing side. Further, a person skilled in the art will appreciate that only one side of the adjunct applicator can include an adjunct, and therefore in other embodiments, an adjunct can be disposed on only one of the cartridge-facing side and the anvil-facing side.

As shown in FIG. 31, an adjunct 1512 is positioned on the elongated base member 1508 and is releasably retained to the elongated base member 1508 via movable attachment elements 1514. The adjunct 1512 has an intended cut line $C_L$ that extends along the longitudinal axis $L_A$ of the adjunct 1512, and thus along the longitudinal axis L of the adjunct applicator 1500. The intended cut line divides the adjunct 1512 into a retaining segment 1516 and a removing segment 1518. The retaining segment 1516 and the removing segment 1518 are similar to the retaining segment 1410 and the removing segment 1412 of adjunct 1400 in FIG. 30, except that a color indicator feature 1520 is printed on the tissue-contacting surface 1518a of the retaining segment 1516. As a result, the color indicator feature 1520 identifies the removing segment 1518 for the user. Further, in use, this color indicator feature 1520 allows a user to choose which side of the adjunct (e.g., relative to the intended cut line $C_L$) stays with the patient and which side of adjunct is removed from the surgical site. In certain embodiment, the color indicator feature can also be used to identify the location of one or more drugs disposed within the adjunct and/or the drug delivery side of the adjunct.

Alternatively, or in addition, the first longitudinal segment 1504 and/or the second longitudinal segment 1506 can include an indicator feature that can be used to identify the retaining segment 1516 and/or removing segments 1518 of the adjunct 1512. For example, as shown in FIG. 31, the first longitudinal segment 1504 of the adjunct applicator 1500 includes the following indicia printed on a surface thereof: "This side stays with patient." Since the retaining segment 1516 is positioned directly adjacent to the first longitudinal segment 1504, this indicia can be used to identify the retaining segment 1516 of the adjunct 1512. As further shown, the second longitudinal segment 1506 of the adjunct applicator 1500 includes the following indicia printed on a surface thereof: "This side goes with specimen." Since the removing segment 1518 is positioned directly adjacent to the second longitudinal segment 1506, this indicia can be used to identify the removing segment 1518 of the adjunct 1512. In other embodiments, only one of the first longitudinal segment and the second longitudinal segment includes an indicator feature. In other embodiments, an indicator feature on either the first longitudinal segment, the second longitudinal segment, or both, can be used to determine the drug delivery side of the adjunct.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A compressible adjunct for use with a surgical cartridge, the compressible adjunct comprising:
   a biocompatible adjunct material configured to be releasably retained on at least one of a staple cartridge and an anvil and configured to be delivered to tissue by deployment of staples in the cartridge, the adjunct material comprising a lattice main structure having at least one absorbable sub-structure formed in the lattice main structure, the at least one absorbable sub-structure configured to control fluid movement through the adjunct material such that the fluid movement impacts healing of tissue adjacent the adjunct material when the adjunct material is in a tissue deployed state;
   wherein the lattice main structure comprises a plurality of unit cells having passageways therethrough, and wherein the at least one absorbable sub-structure comprises at least one microstructure formed in at least one unit cell of the plurality of unit cells for controlling fluid flow through the respective passageway.

2. The adjunct of claim 1, wherein the at least one absorbable sub-structure comprises at least one of an active flow control structure and a passive flow control structure.

3. The adjunct of claim 1, wherein the at least one absorbable sub-structure comprises a plurality of absorbable sub-structures that together control a direction of fluid movement through the adjunct material.

4. The adjunct of claim 1, wherein the plurality of unit cells comprise at least one Schwarz-P structure.

5. The adjunct of claim 1, wherein at least a portion of the plurality of unit cells are configured to deform when the adjunct material is compressed so as to draw fluid into the adjunct material when the adjunct material is in a tissue deployed state, pump fluid out of the adjunct material to tissue adjacent the adjunct material when the adjunct material is in a tissue deployed state, or a combination thereof.

6. The adjunct of claim 1, wherein the plurality of unit cells each comprise at least one internal stopping element that is configured to limit the amount of deformation of the respective unit cell when the adjunct material is being compressed.

7. The adjunct of claim 1, wherein the lattice main structure comprises a plurality of hollow struts, and wherein the at least one absorbable sub-structure is formed in at least one of the hollow struts for controlling fluid flow therethrough.

8. The adjunct of claim 1, wherein the at least one absorbable sub-structure comprises at least one of a duck bill valve, a flapper valve, and micro-passageways formed in a sidewall of the lattice main structure.

9. The adjunct of claim 1, wherein the at least one absorbable sub-structure comprises at least one movable valve that is configured to control fluid movement therethrough.

10. A stapling assembly for use with a surgical stapler, comprising:
   a cartridge having a plurality of staples disposed therein, the plurality of staples being arranged in staple rows and configured to be deployed into tissue; and
   a biocompatible adjunct configured to be releasably retained on the cartridge and configured to be delivered to tissue by deployment of the plurality of staples, the adjunct comprising a lattice macrostructure having a plurality of absorbable microstructures formed therein, each absorbable microstructure being configured to direct, limit, or prevent fluid movement as fluid flows through the lattice macrostructure;
   wherein the plurality of absorbable microstructures comprise at least one of an active flow control structure and a passive flow control structure.

11. The assembly of claim 10, wherein the lattice macrostructure comprises a plurality of Schwarz-P structures having passageways therethrough, and wherein the plurality of absorbable microstructures comprise at least one microfeature formed in at least one Schwarz-P structure of the plurality of Schwarz-P structures for controlling fluid flow through the respective passageway.

12. The assembly of claim 11, wherein at least a portion of the plurality of Schwarz-P structures are configured to deform when the adjunct is compressed so as to draw fluid into the adjunct when the adjunct is in a tissue deployed state, pump fluid out of the adjunct to tissue adjacent the adjunct when the adjunct is in a tissue deployed state, or a combination thereof.

13. The assembly of claim 12, wherein at least a portion of the plurality of Schwarz-P structures are positioned within regions of the adjunct that do not overlap with the staple rows when the adjunct is releasably retained on the cartridge.

14. The assembly of claim 10, wherein the plurality of absorbable microstructures comprise movable valves.

* * * * *